(12) United States Patent
von Hirschheydt et al.

(10) Patent No.: US 7,144,889 B2
(45) Date of Patent: Dec. 5, 2006

(54) TRIARYLIMIDAZOLES

(75) Inventors: Thomas von Hirschheydt, Penzberg (DE); Edgar Voss, Bichl (DE)

(73) Assignee: Hoffman-La Roche Inc., Nutley, NJ (US)

( * ) Notice: Subject to any disclaimer, the term of this patent is extended or adjusted under 35 U.S.C. 154(b) by 92 days.

(21) Appl. No.: 10/959,849

(22) Filed: Oct. 6, 2004

(65) Prior Publication Data

US 2005/0085473 A1    Apr. 21, 2005

(30) Foreign Application Priority Data

Oct. 16, 2003  (EP)  .................. 03023633
Nov. 18, 2003  (EP)  .................. 03026522

(51) Int. Cl.
*C07D 401/14*   (2006.01)
*A61K 31/415*   (2006.01)
*C07D 239/10*   (2006.01)

(52) U.S. Cl. ....................... 514/275; 544/331
(58) Field of Classification Search ............... 544/331; 514/275
See application file for complete search history.

(56) References Cited

U.S. PATENT DOCUMENTS 5,656,644 A    8/1997    Adams et al.
6,610,695 B1   8/2003    Adams et al.

FOREIGN PATENT DOCUMENTS

WO    WO 96/18626    6/1996
WO    WO 01/44154    6/2001
WO    WO 03/087026 A1    10/2003

OTHER PUBLICATIONS

Herynk et al., Medline Abstract (Cancer Research, vol. 63, Issue 11, pp. 2990-2996) Jun. 2003.*
Simone, Oncology: Introduction, Cecil Textbook of Medicine, 20th Edition, vol. 1, pp. 1004-1010, 1996.*
Traxler, Protein Tyrosine Kinase Inhibitors in cancer treatment, Exp. Opin. Ther. Patents, 7(6):571-588, 1997.*
Thomas Von Hirschheydt et al, Synthesis, No. 12, pp. 2062-2065 (2004).

* cited by examiner

*Primary Examiner*—Deepak Rao
(74) *Attorney, Agent, or Firm*—George W. Johnston; Patricia S. Rocha-Tramaloni; Brian C. Remy

(57) ABSTRACT

Compounds of the general formula (I)

are presented and are valuable therapeutics for the treatment of cancer and cancer related diseases.

10 Claims, No Drawings

TRIARYLIMIDAZOLES

This invention relates to new triarylimidazoles and their pharmaceutically acceptable salts. The compounds are protein-tyrosine kinase inhibitors, especially inhibitors of c-met kinase and are therefore excellent therapeutics for the treatment of cancer. The invention relates also to pharmaceutical compositions which contain the new compounds as active agents for the treatment of cancer and cancer related diseases.

BACKGROUND OF THE INVENTION

Protein-tyrosine kinases (PTKs), enzymes that catalyse the transfer of the γ phosphate of ATP to tyrosine residues of protein substrates, are critical components of signalling pathways that control cellular proliferation and differentiation. PTKs can be subdivided into two large families, receptor tyrosine kinases (RTKs) and non-receptor tyrosine kinases (NRTKs). RTKs span the plasma membrane and contain an extra-cellular domain, which binds ligand, and an intracellular portion, which possesses catalytic activity and regulatory sequences. Most RTKs, like the hepatocyte growth factor receptor c-met possess a single polypeptide chain and are monomeric in the absence of ligand. Ligand binding to the extracellular portion of RTKs, leads to dimerisation of monomeric receptors resulting in autophosphorylation of specific tyrosine residues in the cytoplasmic portion (for review see: Blume-Jensen, P., and Hunter, T., Nature 411 (2001) 355–365; Hubbard, S. R., et al., J. Biol. Chem. 273 (1998) 11987–11990; Zwick, E., et al., Trends Mol. Med. 8 (2002) 17–23). In general, tyrosine autophosphorylation either stimulates the intrinsic catalytic kinase activity of the receptor or generates recruitment sites for downstream signalling proteins containing phosphotyrosine-recognition domains, such as the Src homology 2 (SH2) domain or the phosphotyrosine-binding (PTB) domain.

Protein tyrosine kinases play a critical role in intracellular signal transduction pathways leading to diverse cellular responses such as proliferation, apoptosis and differentiation. Consequently these enzymes have become primary targets for the development of novel therapeutics designed to block cancer cell proliferation, metastasis, angiogenesis and promote apoptosis. The strategy that has progressed farthest in clinical development is the use of monoclonal antibodies to target growth factor receptor tyrosine kinases. The use of small molecule tyrosine kinase inhibitors however could have significant theoretical advantages over monoclonal antibodies. Small molecule inhibitors could have better tissue penetration, could have activity against intracellular targets and mutated targets and could be designed to have oral bioavailability. Several lead compounds have shown promising activity against such targets as the EGFR, the vascular endothelial cell growth factor receptor and bcr-abl.

The hepatocyte growth factor receptor c-met was first identified as an activated oncogene in an N-methyl-N'-nitrosoguanidine treated human osteogenic sarcoma cell line (MUNG-HOS) by its ability to transform NIH 3T3 mouse fibroblasts. The receptor encoded by the c-met protooncogene (located on chromosome 7) is a two-chain protein composed of 50 kDa(α) chain disulfide linked to a 145 kda(β) chain in an αβ complex of 190 kDa. The α chain is exposed at the cell surface whilst the β chain spans the cell membrane and possesses an intracellular tyrosine kinase domain. The presence of this intracellular tyrosine kinase domain groups c-met as a member of the receptor tyrosine kinase (RTK) family of cell surface molecules.

Hepatocyte growth factor (HGF), also known as Scatter Factor (SF), is a multifunctional cytokine that elicits diverse responses in different cells and tissues. Since its initial discovery and characterisation HGF/SF has been the subject of intense research, particularly regarding its role in cancer development and progression. Much evidence now points to its role as a regulator of carcinogenesis, cancer invasion and metastasis (for review see: Herynk, M. H., and Radinsky, R., In Vivo 14 (2000) 587–596; Jiang, W., et al., Crit. Rev. Oncol. Hematol. 29 (1999) 209–248; Longati, P., et al., Curr. Drug Targets 2 (2001) 41–55; Maulik, G., et al., Cytokine Growth Factor Rev. 13 (2002) 41–59; Parr, C., and Jiang, W. G., Histol. Histopathol. 16 (2001) 251–268.

HGF/SF binds to and induces tyrosine phosphorylation of the mature c-met receptor β chain. Such events are thought to promote binding of intracellular signalling proteins containing src homology (SH) regions such as PLC-γ, Ras-GAP, PI-3 kinase $pp60^{c-src}$ and the GRB-2 Socs complex to the activated receptor. Each SH2-containing protein may activate a different subset of signalling phosphopeptides thus eliciting different responses within the cell.

C-met mutations have been well-described in hereditary and sporadic human papillary renal carcinomas and have been reported in ovarian cancer, childhood hepatocellular carcinoma, metastatic head and neck squamous cell carcinomas, and gastric cancer. C-met is also over-expressed in both non-small cell lung cancer and small cell lung cancer cells, in breast, colon and prostate tumors. Since c-met appears to play an important role in oncogenesis of a variety of tumors, various inhibition strategies have been employed to therapeutically target this receptor tyrosine kinase.

The usefulness of inhibiting the protein-tyrosine kinase c-met for inhibiting tumor growth and invasion has been shown in many well documented preclinical experiments (e.g.: Abounader, R., et al., J. Natl. Cancer Inst. 91 (1999) 1548–1556; Laterra, J., et al., Lab. Invest. 76 (1997) 565–577; Tomioka, D., Cancer Res. 61 (2001) 7518–7524; Wang, R., et al., J. Cell Biol. 153 (2001) 1023–1033).

WO 96/18626 describes inhibitors of tyrosine kinases and c-met kinase which are derivatives of 2-(2,6-dichlorophenyl)-4-phenyl-5-(pyridin-4yl)-1H-imidazole (examples 5, 6 and 55). However they show unfavorable cytochrome P450 interactions.

It has now been found that the compounds according to this invention avoid this disadvantage and are potent inhibitors of c-met kinase with good solubility.

SUMMARY OF THE INVENTION

The invention relates to compounds of the general formula (I)

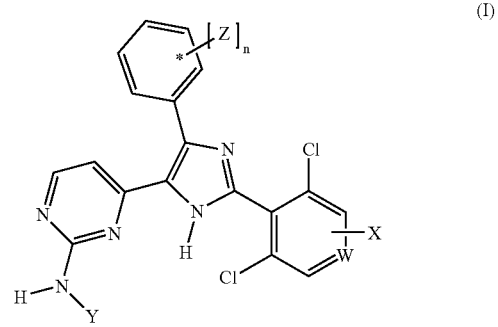

wherein W, X, Y and Z are as described herewithin.

It was surprisingly found that the pharmaceutical and anti-tumorigenic activities, due to the c-met inhibition of the compounds according to this invention are especially provided by the presence of a 2,6-dichlorophenyl or -pyridyl residue in 2-position of the imidazole ring.

DETAILED DESCRIPTION OF THE INVENTION

The present invention relates to new compounds of the formula

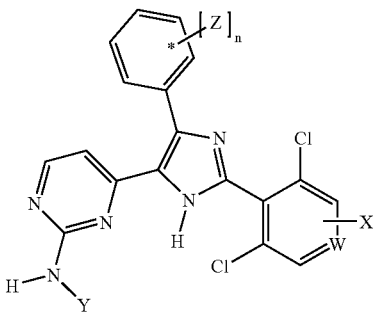

(I)

wherein
W is —N═; and
X is hydrogen;
Y is hydrogen or a 1 group $A^2$—R;
$A^2$ is $C_1$–$C_5$-alkylene, which may be optionally substituted by $C_1$–$C_6$-alkyl; phenyl or by hydroxy;
R represents hydroxy; linear or branched $C_1$–$C_6$-alkoxy; amino; dimethylamino; diethylamino; t-butyloxycarbonylamino; carboxyl; $C_1$–$C_6$-alkoxycarbonyl; triazolyl; cyano; piperidino; 1-pyrrolidinyl; morpholino; 4-methylpiperazin-1-yl; O—$A^1$NR$^3$R$^4$; S—$A^1$—NR$^3$R$^4$; 4-carboxyphenyl; furan-3-yl; thiophen-2-yl or 3-methylthiophen-2-yl;
n is 1 or 2; and
Z represents one or two substituents independently selected from the group consisting of halogen; hydroxy; allyloxy; methyl; $C_1$–$C_3$-alkoxy, which are optionally substituted with pyridinyl; methoxymethoxy; (2-methoxyethoxy)methyloxy; methylthio; ethoxymethoxy; methylendioxy; ethynyl; trimethylsilylethynyl and benzyloxy which is optionally substituted by halogen; methoxy; cyano; nitro; methylendioxy; carboxy or ethoxy;
or alternatively
W is —CH═; and
X is hydrogen; OR$^1$; SR$^2$; (SO)R$^2$; (SO$_2$)R$^2$; CH$_2$—S—CH$_2$—C(O)$_2$—CH$_2$—CH$_3$; CH$_2$—S—(CH$_2$)$_2$—OH or a group $A^1$—Q;
$A^1$ represents a $C_1$–$C_3$-alkylene group;
Q is OR$^1$; SR$^2$; SOR$^2$; SO$_2$R$^2$; NR$^3$R$^4$; NHCH$_2$CH$_2$NR$^3$R$^4$ or halogen;
$R^1$ is selected from the group consisting of hydrogen; $C_1$–$C_3$-alkyl; allyl; dimethylphosphonylmethyl; 2,3-epoxy-1-propyl; (R)-2,3-dihydroxy-1-propyl; (S)-2,3-dihydroxy-1-propyl; 1,3-dihydroxy-2-propyl; 3-hydroxy-2-hydroxymethyl-1-propyl; 2-methoxyethoxymethyl; 2,2-dimethyl-1,3-dioxolan-4-ylmethyl or a group $A^1$—Q$^1$;
$Q^1$ represents $C_1$–$C_2$-alkoxy; cyano; carboxyl; $C_1$–$C_6$-alkoxycarbonyl; carboxamide; —CO—NR$^3$R$^4$; $C_1$–$C_6$-alkylsulfanyl; $C_1$–$C_6$-alkylsulfenyl; $C_1$–$C_6$-alkylsulfonyl and
in case that $A^1$ represents an 1,2-ethylen- or 1,3-propylen group, $Q^1$ is hydroxy or NR$^3$R$^4$;

$R^2$ is $C_1$–$C_6$-alkyl; dimethylphosphonylmethyl; 2,3-epoxy-1-propyl; 2,3-dihydroxy-1-propyl; 2,2-dimethyl-1,3-dioxolan-4-ylmethyl or $A^1$13 $Q^1$;
$R^3$, $R^4$ are independently selected from the group consisting of hydrogen; $C_1$–$C_6$-alkyl or together form a 5 to 7 membered, saturated or unsaturated ring, optionally substituted by a methyl group and containing one or two heteroatoms, independently selected from N or O;
Y is hydrogen or a group $A^2$—R;
$A^2$ is $C_1$–$C_5$-alkylene, which may be optionally substituted by $C_1$–$C_6$-alkyl; phenyl or by hydroxy;
R represents hydroxy; linear or branched $C_1$–$C_6$-alkoxy; amino; dimethylamino; diethylamino; t-butyloxycarbonylamino; carboxyl; $C_1$–$C_6$-alkoxycarbonyl; triazolyl; cyano; piperidino; 1-pyrrolidinyl; morpholino; 4-methylpiperazin-1-yl; O—$A^1$—NR$^3$R$^4$; S—$A^1$—NR $^3$R$^4$; 4-carboxyphenyl; furan-3-yl; thiophen-2-yl or 3-methylthiophen-2-yl;
n is 1 or 2; and
Z represents $C_1$–$C_3$-alkoxy, substituted with pyridinyl if n is 1; and
if n is 2, one substituent represents $C_1$–$C_3$-alkoxy, substituted with pyridinyl, and the second substituent being independently selected from the group consisting of halogen; hydroxy; allyloxy; methyl; $C_1$–$C_3$-alkoxy; methoxymethoxy; (2-methoxyethoxy)methyloxy; methylthio; ethoxymethoxy; methylendioxy; ethynyl; trimethylsilylethynyl; and
pharmaceutically acceptable salts thereof Preferred $C_1$–$C_6$-alkyl groups with regard to $R^1$, $R^2$, $R^3$, $R^4$ and $A^2$ are methyl, ethyl and propyl.

Preferred $C_1$–$C_6$-alkoxy groups with regard to $Q^1$, R and Z are methoxy, ethoxy or isopropyloxy.

Preferred ring systems, formed by $R^3$ and $R^4$ together represent 1-pyrrolidinyl-, piperidino-, morpholino- or 4-methylpiperazin-1-yl.

Preferably X=$A^1$—Q represents —CH$_2$OH or —CH$_2$—CH$_2$—OH.

Preferably X═—O—$A^1$—Q$^1$ is —O—CH$_2$—CH$_2$—OH; —O—CH$_2$—COOH or —O—CH$_2$—CN.

Preferred groups for Y=$A^2$—R are 2-hydroxyethyl; 3-hydroxypropyl, 2-methoxyethyl;

3-methoxypropyl; (R)-2,3-dihydroxy-1-propyl; (S)-2,3-dihydroxy-1-propyl; (R)-3-hydroxybutyl; (S)-3-hydroxybutyl; 2-morpholinoethyl; 3-morpholinopropyl; (CH$_2$)$_3$ COOH;

2-(4-methylpiperazin-1-yl)ethyl; 3-Hydroxy-2,2-dimethylpropyl;

3-hydroxy-1-phenylpropyl; 3-tert-butyloxyethyl; 2-aminoethyl; 3-aminopropyl;

4-aminobutyl; 2-(N,N-dimethylamino)ethyl; 3-(N,N-dimethylamino)propyl;

3-(pyrrolidin-1-yl)propyl; CH$_2$COOH; (CH$_2$)$_2$COOH; CH(C$_2$H$_5$)COOH;

(CH$_2$)$_3$COOC(CH$_3$)$_3$; (CH$_2$)$_2$—N—COOC(CH$_3$)$_3$; (CH$_2$)$_3$—N—COOC(CH$_3$)$_3$; (CH$_2$)$_2$—O—(CH$_2$)$_2$—N(CH$_3$)$_2$; (CH$_2$)$_2$—O—(CH$_2$)$_2$—NH$_2$; (CH$_2$)$_2$—S—(CH$_2$)$_2$—N(CH$_3$)$_2$;(CH$_2$)$_2$—S—(CH$_2$)$_3$—N(CH$_3$)$_2$;

(CH$_2$)$_3$—S—(CH$_2$)$_2$—N(CH$_3$)$_2$; (CH$_2$)$_3$—S—(CH$_2$)$_3$—N(CH$_3$)$_2$; (1,2,4-triazol-1-yl)ethyl; 3-(1,2,4-triazol-3-yl) propyl;

Halogen is fluorine, chlorine, bromine or iodine.

Preferably n is 1, and said substituent Z is located in the 3- or 4-position. If Z represents methoxy which is substituted with pyridinyl; benzyloxy or a substituted benzyloxy group, Z is preferably located in the 3-position.

Especially preferred are compounds of the general formula (I) and pharmaceutically acceptable salts thereof, wherein W is —N=; Z is selected from the group consisting of 3-chloro; 4-chloro; 3-bromo; 3-iodo; 3-ethynyl; 3-methoxymethoxy; 3-(2-methoxyethoxy)methyloxy; 3-methylthio; 3-ethoxymethoxy; 3,4-methylendioxy or 3-benzyloxy which is optionally substituted by halogen; methoxy; cyano; nitro; methylendioxy; carboxy or ethoxy.

Also especially preferred are compounds of the general formula (I), wherein

W is —N=;

X is hydrogen;

Y represents 2-hydroxyethyl; 3-hydroxypropyl; 2-methoxyethyl; 3-methoxypropyl; (R)-2,3-dihydroxy-1-propyl; (S)-2,3-dihydroxy-1-propyl; (R)-3-hydroxybutyl; (S)-3-hydroxybutyl; 3-Hydroxy-2,2-dimethylpropyl; 2-morpholinoethyl;

3-morpholinopropyl; 2-(4-methylpiperazin-1-yl)ethyl; 3-hydroxy-1-phenylpropyl;

2-aminoethyl; 3-aminopropyl; 4-aminobutyl; 2-(N,N-dimethylamino)ethyl; 3-(N,N-dimethylamino)propyl; 3-(pyrrolidin-1-yl)propyl; $CH_2COOH$; $(CH_2)_2COOH$; $(CH_2)_3COOH$; $CH(C_2H_5)COOH$; $(CH_2)_2$—O—$(CH_2)_2$—N$(CH_3)_2$; $(CH_2)_2$—O—$(CH_2)_2$—$NH_2$; $(CH_2)_2$—S—$(CH_2)_2$—N$(CH_3)_2$; $(CH_2)_2$—S—$(CH_2)_3$—N$(CH_3)_2$; $(CH_2)_3$—S—$(CH_2)_2$—N$(CH_3)_2$ or $(CH_2)_3$—S—$(CH_2)_3$—N$(CH_3)_2$;

n is 1; and

Z is selected from the group consisting of 3-chloro; 4-chloro; 3-bromo; 3-iodo; 3-ethynyl; 3-methoxymethoxy or 3-benzyloxy which is optionally substituted by halogen; methoxy; cyano; nitro; methylendioxy; carboxy or ethoxy.

Also especially preferred are compounds of the general formula (I), wherein

W is —N=;

X is hydrogen;

Y is 2-hydroxyethyl; 3-hydroxypropyl; (R)-2,3-dihydroxy-1-propyl; (S)-2,3-dihydroxy-1-propyl; 2-morpholinoethyl; 3-morpholinopropyl; 2-(4-methylpiperazin-1-yl)ethyl; 2-aminoethyl; 3-aminopropyl; 2-(N,N-dimethylamino)ethyl; 3-(N,N-dimethylamino)propyl or 3-(pyrrolidin-1-yl)propyl;

n is 1; and

Z is selected from the group consisting of 3-chloro; 4-chloro; 3-bromo; 3-iodo; 3-ethynyl; 3-methoxymethoxy or 3-benzyloxy which is optionally substituted by halogen; methoxy or cyano.

Such a compound is for example:

2-(3,5-dichloropyridin-4-yl)-4-(3-benzyloxyphenyl)-5-(2-[3-hydroxypropyl-amino]pyrimidin-4-yl)-N-1H-imidazole A further embodiment of the present invention are the compounds of formula (I), wherein W is —CH=;

X is hydrogen; $OR^1$; $SR^2$; $(SO)R^2$; $(SO_2)R^2$; $CH_2$—S—$CH_2$—$C(O)_2$—$CH_2$—$CH_3$; $CH_2$—S—$(CH_2)_2$—OH or a group $A^1$—Q;

$A^1$ represents a $C_1$–$C_3$-alkylen group;

Q is $OR^1$; $SR^2$; $SOR^2$; $SO_2R^2$; $NR^3R^4$; $NHCH_2CH_2NR^3R^4$ or halogen;

$R^1$ is selected from the group consisting of hydrogen; $C_1$–$C_3$-alkyl; allyl; dimethylphosphonylmethyl; 2,3-epoxy-1-propyl; (R)-2,3-dihydroxy-1-propyl; (S)-2,3-dihydroxy-1-propyl; 1,3-dihydroxy-2-propyl; 3-hydroxy-2-hydroxymethyl-1-propyl; 2-methoxyethoxymethyl; 2,2-dimethyl-1,3-dioxolan-4-ylmethyl or a group $A^1$—$Q^1$;

$Q^1$ represents $C_1$–$C_2$-alkoxy; cyano; carboxyl; $C_1$–$C_6$-alkoxycarbonyl; carboxamide; —CO—$NR^3R^4$; $C_1$–$C_6$-alkylsulfanyl; $C_1$–$C_6$-alkylsulfenyl; $C_1$–$C_6$-alkylsulfonyl and in case that $A^1$ represents an 1,2-ethylen- or 1,3-propylen group, $Q^1$ is hydroxy or $NR^3R^4$;

$R^2$ is $C_1$–$C_6$-alkyl; dimethylphosphonylmethyl; 2,3-epoxy-1-propyl; 2,3-dihydroxy-1-propyl; 2,2-dimethyl-1,3-dioxolan-4-ylmethyl or $A^1$—$Q^1$;

$R^3$, $R^4$ are independently selected from the group consisting of hydrogen; $C_1$–$C_6$-alkyl or together form a 5 to 7 membered, saturated or unsaturated ring, optionally substituted by a methyl group and containing one or two heteroatoms, independently selected from N or O;

Y is 3-hydroxypropyl; and

Z is 3-benzyloxy which is optionally substituted by halogen; methoxy or cyano.

Still another embodiment of the invention are the compounds of formula (I), wherein W is —CH=;

X is hydrogen; or $OR^1$;

$R^1$ is selected from the group consisting of hydrogen; $C_1$–$C_3$-alkyl; allyl; dimethylphosphonylmethyl; 2,3-epoxy-1-propyl; (R)-2,3-dihydroxy-1-propyl; (S)-2,3-dihydroxy-1-propyl; 1,3-dihydroxy-2-propyl; 3-hydroxy-2-hydroxymethyl-1-propyl; 2-methoxyethoxymethyl; 2,2-dimethyl-1,3-dioxolan-4-ylmethyl or a group $A^1$—$Q^1$;

$A^1$ represents a $C_1$–$C_3$-alkylen group;

$Q^1$ represents $C_1$–$C_2$-alkoxy; cyano; carboxyl; $C_1$–$C_6$-alkoxycarbonyl; carboxamide; $C_1$–$C_6$-alkylsulfanyl; $C_1$–$C_6$-alkylsulfenyl; $C_1$–$C_6$-alkylsulfonyl and in case that $A^1$ represents an 1,2-ethylen- or 1,3-propylen group, $Q^1$ is hydroxy;

Y is 3-hydroxypropyl; and

Z is 3-benzyloxy.

A further embodiment of the present invention are the compounds of formula (I), wherein W is —CH=;

X is hydrogen; $OR^1$; $SR^2$; $(SO)R^2$; $(SO_2)R^2$; $CH_2$—S—$CH_2$—$C(O)_2$—$CH_2$—$CH_3$; $CH_2$—S—$(CH_2)_2$—OH or a group $A^1$—Q;

$A^1$ represents a $C_1$–$C_3$-alkylene group;

Q is $OR^1$; $SR^2$; $SOR^2$; $SO_2R^2$; $NR^3R^4$; $NHCH_2CH_2NR^3R^4$ or halogen;

$R^1$ is selected from the group consisting of hydrogen; $C_1$–$C_3$-alkyl; allyl; dimethylphosphonylmethyl; 2,3-epoxy-1-propyl; (R)-2,3-dihydroxy-1-propyl; (S)-2,3-dihydroxy-1-propyl; 1,3-dihydroxy-2-propyl; 3-hydroxy-2-hydroxymethyl-1-propyl; 2-methoxyethoxymethyl; 2,2-dimethyl-1,3-dioxolan-4-ylmethyl or a group $A^1$—$Q^1$;

$Q^1$ represents $C_1$–$C_2$-alkoxy; cyano; carboxyl; $C_1$–$C_6$-alkoxycarbonyl; carboxamide; —CO—$NR^3R^4$; $C_1$–$C_6$-alkylsulfanyl; $C_1$–$C_6$-alkylsulfenyl; $C_1$–$C_6$-alkylsulfonyl and in case that $A^1$ represents an 1,2-ethylen- or 1,3-propylen group, $Q^1$ is hydroxy or $NR^3R^4$;

$R^2$ is $C_1$–$C_6$-alkyl; dimethylphosphonylmethyl; 2,3-epoxy-1-propyl; 2,3-dihydroxy-1-propyl; 2,2-dimethyl-1,3-dioxolan-4-ylmethyl or $A^1$—$Q^1$;

$R^3$, $R^4$ are independently selected from the group consisting of hydrogen; $C_1$–$C_6$-alkyl or together form a 5 to 7 membered, saturated or unsaturated ring, optionally substituted by a methyl group and containing one or two heteroatoms, independently selected from N or O;

Y is hydrogen or a group $A^2$—R;

$A^2$ is $C_1$–$C_5$-alkylene, which may be optionally substituted by $C_1$–$C_6$-alkyl; phenyl or by hydroxy;

R represents hydroxy; linear or branched $C_1$–$C_6$-alkoxy; amino; dimethylamino; diethylamino; t-butyloxycarbonylamino; carboxyl; $C_1$–$C_6$-alkoxycarbonyl; triazolyl; cyano; piperidino; 1-pyrrolidinyl; morpholino; 4-methylpiperazin-1-yl; O—$A^1$—$NR^3R^4$; S—$A^1$—$NR^3R^4$; 4-carboxyphenyl; furan-3-yl; thiophen-2-yl or 3-methylthiophen-2-yl;

n is 1; and

Z represents $C_1$–$C_3$-alkoxy, which is substituted with pyridinyl.

Still another embodiment of the present invention are the compounds of formula (I), wherein W is —CH=;

X is hydrogen; $OR^1$; $SR^2$; $(SO)R^2$; $(SO_2)R^2$; $CH_2$—S—$CH_2$—$C(O)_2$—$CH_2$—$CH_3$; $CH_2$—S—$(CH_2)_2$—OH or a group $A^1$—Q;

$A^1$ represents a $C_1$–$C_3$-alkylene group;

Q is $OR^1$; $SR^2$; $SOR^2$; $SO_2R^2$; $NR^3R^4$; $NHCH_2CH_2NR^3R^4$ or halogen;

$R^1$ is selected from the group consisting of hydrogen; $C_1$–$C_3$-alkyl; allyl; dimethylphosphonylmethyl; 2,3-epoxy-1-propyl; (R)-2,3-dihydroxy-1-propyl; (S)-2,3-dihydroxy-1-propyl; 1,3-dihydroxy-2-propyl; 3-hydroxy-2-hydroxymethyl-1-propyl; 2-methoxyethoxymethyl; 2,2-dimethyl-1,3-dioxolan-4-ylmethyl or a group $A^1$—$Q^1$;

$Q^1$ represents $C_1$–$C_2$-alkoxy; cyano; carboxyl; $C_1$–$C_6$-alkoxycarbonyl; carboxamide; —CO—$NR^3R^4$; $C_1$–$C_6$-alkylsulfanyl; $C_1$–$C_6$-alkylsulfenyl; $C_1$–$C_6$-alkylsulfonyl and in case that $A^1$ represents an 1,2-ethylen- or 1,3-propylen group, $Q^1$ is hydroxy or $NR^3R^4$;

$R^2$ is $C_1$–$C_6$-alkyl; dimethylphosphonylmethyl; 2,3-epoxy-1-propyl; 2,3-dihydroxy-1-propyl; 2,2-dimethyl-1,3-dioxolan-4-ylmethyl or $A^1$—$Q^1$;

$R^3$, $R^4$ are independently selected from the group consisting of hydrogen; $C_1$–$C_6$-alkyl or together form a 5 to 7 membered, saturated or unsaturated ring, optionally substituted by a methyl group and containing one or two heteroatoms, independently selected from N or O;

Y is 3-hydroxypropyl;

n is 1; and

Z is pyridin-2-ylmethoxy; pyridin-3-ylmethoxy or pyridin-4-ylmethoxy.

Such compounds are for example:

2-(2,6-dichloro-4-[2-hydroxyethoxy]phenyl)-4-(3-(4-pyridinylmethyloxy)phenyl)-5-(2-[3-hydroxypropylamino]pyrimidin-4-yl)-N-1H-imidazole, 2-(2,6-dichloro-4-[2-hydroxyethoxy]phenyl)-4-(3-(3-pyridinylmethyloxy)phenyl)-5-(2-[3-hydroxypropylamino]pyrimidin-4-yl)-N-1H-imidazole, and 2-(2,6-dichloro-4-[2-hydroxyethoxy]phenyl)-4-(3-(2-pyridinylmethyloxy)phenyl)-5-(2-[3-hydroxypropylamino]pyrimidin-4-yl)-N-1H-imidazole.

Formula (I) represents 2-(2,6-dichlorophenyl)-4-phenyl-5-(4-pyrimidinyl)-1H-imidazoles which are the tautomers of 2-(2,6-dichlorophenyl)-5-phenyl-4-(4-pyrimidinyl)-1H-imidazoles. Both tautomers represent the same structure, their nomenclature may be used interchangeably and both tautomers are part of the invention. The compounds of the present invention may contain one or more asymmetric carbon atoms and may occur as racemates, racemic mixtures, and as individual diastereomers, with all possible isomers, including optical isomers, being included within the scope of the present invention.

Compounds of the general formula (I) can be prepared by reacting a compound of the general formula (VI) or (VII) with an amine Y—$NH_2$, wherein W, X, Y, n and Z have the significance as defined herein before, at a temperature in the range of 80 to 180° C. and subsequent isolation of said compound. Preferably stoichiometric amounts or an excess of said amines are used. The reaction can be performed without solvent or in a solvent like dioxane, dimethoxyethane or toluene.

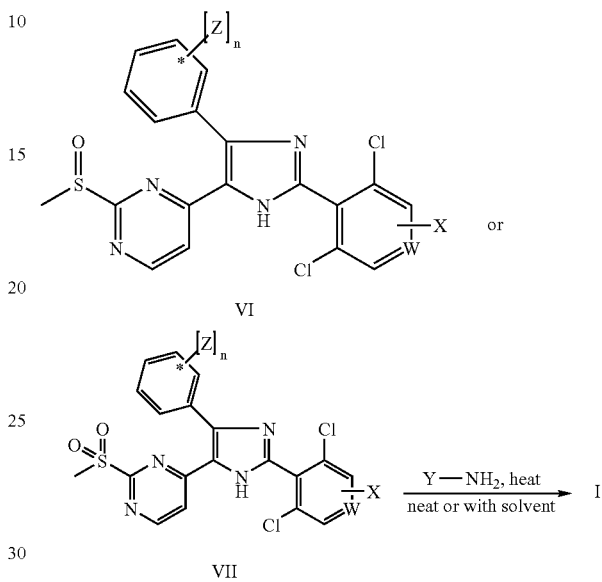

Compounds of the general formula (VI) and (VII) can be obtained by oxidation of the sulfide group of the thioethers, described by the general formula (V). To obtain the sulfoxides of the general formula (VI) the oxidation is preferably carried out by using 3-chloroperbenzoic acid. For the synthesis of the sulfones of the general formula (VII) oxone™ is preferably used.

The thioethers of the general formula (V)

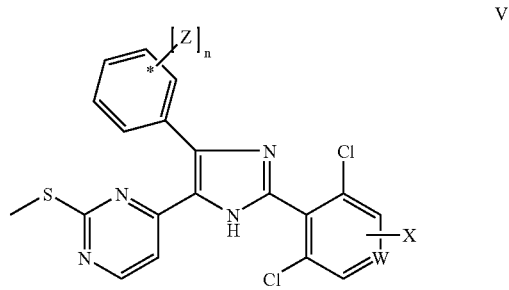

can be obtained by N-deoxygenation of compounds of the general formula (IV). This reaction is preferably carried out using ethyl bromoacetate in the presence of triethylamine (Somei, M., and Tsuchiya, M., Chem. Pharm. Bull. 29 (1981) 3145–3157). Alternatively, this reduction can be achieved by the use of triethylphosphite in dimethylformamide.

A compound of the general formula (IV) can be obtained by reacting a compound of the general formula (III) with a compound of the general formula (II), wherein the substituents W, X and Z have the significance as defined hereinbefore. This reaction is a condensation and is preferably carried out in the presence of ammonia, using methods which are known for other aldehydes.

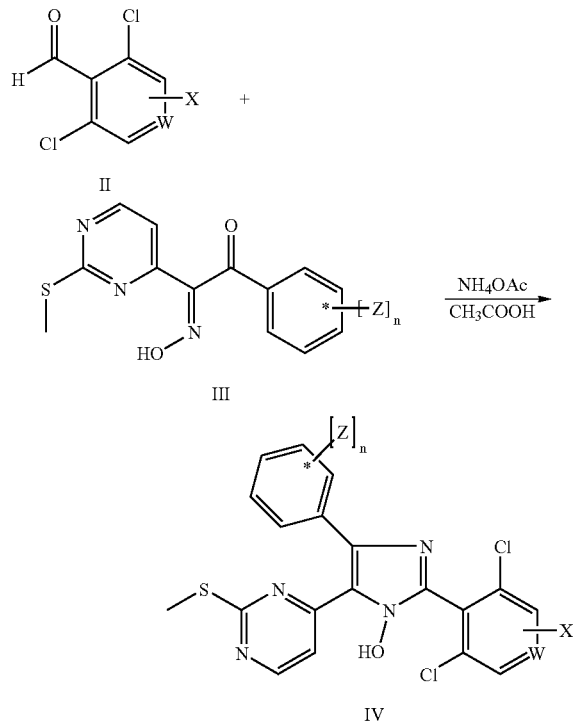

A further embodiment of the invention is the use of a compound of the general formula (II), wherein the substituent X has the significance as defined hereinbefore, for the manufacture of a compound of the general formula (I) as described in the above-mentioned process.

The 2,6-dichlorobenzaldehydes are valuable intermediates for the manufacture of the compounds of the general formula (I) according to the invention. 2,6-dichloro-3-hydroxybenzaldehyde and 2,6-dichloro-4-hydroxybenzaldehyde are known from the state of the art. The 2,6-dichloro-3-hydroxybenzaldehyde has been synthesized from 3-hydroxybenzaldehyde (Gust, R., and Schoenenberg, H., Eur. J. Med. Chem. 28 (1993) 103–115), but this requires the use of highly toxic chlorine gas and leads to side products because of overoxidation. The procedure disclosed in this invention (example A2) avoids these disadvantages. 2,6-dichloro-4-hydroxybenzaldehyde can be prepared from 3,5-dichlorophenol by either a Reimer-Tiemann reaction (Baldwin, J. J., et al., J. Med. Chem. 22 (1979) 687–693) or by a bromination/Grignard sequence (WO 01/44154). The Reimer-Tiemann procedure does not allow an economically preparation due to very low yields (<4%); in addition, the required use of chloroform causes substantial ecological issues. The other known reaction via a bromination/Grignard sequence requires 4 steps totally, including stoichiometric bromination with bromine and the use of toxic chloromethyl methyl ether to protect the phenol. In addition, the total yield is only 40%.

This invention provides an improved process for the manufacture of 2,6-dichloro-3-hydroxybenzaldehyde and 2,6-dichloro-4-hydroxybenzaldehyde. This process is characterized by the metallation of protected 2,4-dichlorophenol or 3,5-dichlorophenol with a lithium base, followed by reaction with an ester or amide of formic acid and the deprotection and isolation of said compounds. A suitable lithium base is methyllithium, n-butyllithium, sec-butyllithium, t-butyllithium, lithiumdiisopropylamide or lithium bistrimethylsilylamide, prefered is butyllithium. An appropriate solvent is diethyl ether, tetrahydrofurane or 1,2-dimethoxyethane, preferred is tetrahydrofurane. The metallation step is performed at −100° C. to −60° C., preferably at −80° C. to −70° C. Suitable protecting groups are triisopropylsilanyl, t-butyldimethylsilanyl or phenyldimethylsilanyl, prefered is triiso-propylsilanyl. Suitable derivatives of formic acid are methyl formate, ethylformate, dimethylformamide or N-formylpiperidine, preferred is dimethylformamide. This procedure can also be applied for the manufacture of 2,6-dichloro-3-hydroxymethylbenzaldehyde and 2,6-dichloro-4-hydroxymethyl-benzaldehyde according to this invention.

The term "pharmaceutically acceptable salt" as used herein before refers to conventional acid-addition salts or base-addition salts that retain the biological effectiveness and properties of the compounds of formula (I) and are formed from suitable non-toxic organic or inorganic acids or organic or inorganic bases. Sample acid-addition salts include those derived from inorganic acids such as hydrochloric acid, hydrobromic acid, hydroiodic acid, sulfuric acid, sulfamic acid, phosphoric acid and nitric acid, and those derived from organic acids such as p-toluenesulfonic acid, salicylic acid, methanesulfonic acid, oxalic acid, succinic acid, citric acid, malic acid, lactic acid, fumaric acid, and the like. Sample base-addition salts include those derived from ammonium, potassium, sodium and, quaternary ammonium hydroxides, such as for example, tetramethylammonium hydroxide. The chemical modification of a pharmaceutical compound (i.e., a drug) into a salt is a technique well known to pharmaceutical chemists to obtain improved physical and chemical stability, hygroscopicity, flowability and solubility of compounds (see, e.g., H. Ansel et. al., Pharmaceutical Dosage Forms and Drug Delivery Systems, 6th ed., (1995), pp. 196 and 1456–1457.

The compounds of formula (I) and the pharmaceutically acceptable salts of the compounds of formula (I) can be used as medicaments, e.g. in the form of pharmaceutical preparations. The pharmaceutical preparations can be administered orally, e.g., in the form of tablets, coated tablets, dragées, hard and soft gelatine capsules, solutions, emulsions or suspensions. The administration can, however, also be effected rectally, e.g. in the form of suppositories, parenterally, e.g. in the form of injection solutions.

The compounds of formula (I) can be processed with pharmaceutically inert, inorganic or organic carriers for the production of pharmaceutical preparations. Lactose, corn starch or derivatives thereof, talc, stearic acids or its salts and the like can be used, for example, as such carriers for tablets, coated tablets, dragées and hard gelatine capsules. Suitable carriers for soft gelatine capsules are, for example, vegetable oils, waxes, fats, semi-solid and liquid polyols and the like. Depending on the nature of the active substance no carriers are, however, usually required in the case of soft gelatine capsules. Suitable carriers for the production of solutions and syrups are, for example, water, polyols, glycerol, vegetable oil and the like. Suitable carriers for suppositories are, for example, natural or hardened oils, waxes, fats, semi-liquid or liquid polyols and the like.

The pharmaceutical preparations can, moreover, contain preservatives, solubilizers, stabilizers, wetting agents, emulsifiers, sweeteners, colorants, flavorants, salts for varying the osmotic pressure, buffers, masking agents or antioxidants. They can also contain still other therapeutically valuable substances.

Medicaments containing a compound of formula (I) or a pharmaceutically acceptable salt thereof and a therapeutically inert carrier are also an object of the present invention, as is a process for their production, which comprises bringing one or more compounds of formula (I) and/or pharmaceutically acceptable salts and, if desired, one or more other therapeutically valuable substances into a galenical administration form together with one or more therapeutically inert carriers.

Because of their activity as tyrosine kinase inhibitors, preferably of c-met kinase, compounds of the general formula (I) are valuable ingredients of therapeutics aiming at the treatment of cancer and other diseases that correspond with enhanced expression of the c-met receptor or related kinase receptors.

Therefore the dosage of a compound according to this invention can vary within wide limits and will also have to be adjusted to the individual requirements in each particular case. In the case of oral administration the dosage for adults can vary from about 0.01 mg to about 1000 mg per day of a compound of general formula (I) or of the corresponding amount of a pharmaceutically acceptable salt thereof. The daily dosage may be administered as single dose or in divided doses and, in addition, the upper limit can also be exceeded when this is found to be indicated.

The following examples and preparations illustrate the invention but are not intended to limit its scope.

EXAMPLES

A Synthesis of substituted 2,6-dichlorobenzaldehydes

Example A1

2,6-dichloro-4-hydroxybenzaldehyde (A1)

Preparation of 3,5-dichlorotriisopropylsilyloxybenzene (A1.1)

To a solution of 200 g 3,5-dichlorophenol and 330 ml 2,6-lutidine in 3.0 l dry $CH_2Cl_2$ 400 g triisopropyl-silyltriflate was added at 0° C. within 1 h and the mixture was stirred for additional 3 hours at this temperature. After hydrolysis with 1.0 l water the organic layer was washed with saturated NaCl, dried over $MgSO_4$ and evaporated to dryness (70° C./80 mbar). The residue was taken up in petroleum ether and filtrated through Silica to yield 360 g (92%) A1.1 as colorless oil.

$^1$H-NMR (250 MHz, $CDCl_3$) δ=1.03–1.15 (m, 18 H, $CH_3$); 1.16–1.35 (m, 3 H CH); 6.73–6.80 (m, 2 H, $CH_{arom.}$); 6.92–6.98 (m, 1 H, $CH_{arom.}$);

$^{13}$C-NMR (62.9 MHz, $CDCl_3$) δ=12.7 (CH); 18.0 ($CH_3$); 119.0, 121.6 ($CH_{arom.}$); 135.2, 157.4 ($C_{arom.}$)

Preparation of 2,6-dichloro-4-hydroxybenzaldehyde (A1) and 2,6-dichloro-4-triisopropylsilyloxy-benzaldehyde (A1.2)

To a solution of 360 g A1.1 in 2.6 l dry tetrahydrofuran 440 ml n-BuLi (2.7 M in hexane) was added under nitrogen keeping the temperature below –65° C. After stirring for 2 h at –70° C. 120 ml dry dimethylformamide was added keeping the temperature below –65° C. The mixture was allowed to warm up to room temperature overnight. After addition of 700 ml 4 M HCl the mixture was stirred vigorously for 1 h at room temperature. Then the phases were separated (addition of solid NaCl may be necessary) and the organic layer was dried over sodium sulphate and was reduced in vacuo. Recrystallization of the precipitate from toluene/tetrahydrofuran yielded 154 g (70%) A1, m.p. 229–230° C.

$^1$H-NMR (250 MHz, $DMSO-D_6$) δ=6.94 (s, 2 H, $CH_{arom.}$); 10.25 (s, 1 H, CH=O), 11.46 (s (br), 1 H, OH)

$^{13}$C-NMR (62.9 MHz, $DMSO-D_6$) δ=117.0 ($CH_{arom.}$); 120.7, 137.8, 162.1 ($C_{arom.}$); 187.2 (CH=O)

Example A2

Preparation of ethyl (3,5-dichloro-4-formylphenoxy)acetate (A2)

A mixture of 2.87 g (15 mmol) A1, 2.76 g (16.5 mmol) ethyl bromoacetate and 2.90 g (21 mmol) potassium carbonate in 50 ml dry acetone were stirred for 3 h at 60° C. After filtration and removal of the solvent the residue was purified by column chromatography on Silica (ethyl acetate/methanol 100:2). Yield: 3.5.5 g (86 %) A2, colorless solid.

$^1$H-NMR (250 MHz, $CDCl_3$): δ=1.32 (t, 7.2 Hz, 3 H, $CH_3$); 4.30 (q, 7.2 Hz, 2 H, $CH_2$); 4.68 (s, 2 H, $CH_2$); 6.92 (s, 2 H, $CH_{arom.}$); 10.41 (s, 1 H, CH=O).

$^{13}$C-NMR (62.9 MHz, $CDCl_3$): δ=14.3 ($CH_3$); 62.1, 65.5 ($CH_2$); 116.4 ($CH_{arom.}$); 123.8, 139.2, 160.9 ($C_{arom.}$); 167.3 (C=O); 187.8 (CH=O).

B Synthesis of the "Weinreb"-type amides

Example B1

3-benzyloxy-N-methoxy-N-methylbenzamide (B1)

To a suspension of 136.8 g (0.60 mol) 3-benzyloxybenzoic acid in 1200 ml dichloromethane 60.6 g (0.6 mol) triethylamine was added at 10° C. A solution of 64.8 g (0.60 mol) ethyl chloroformiate in 100 ml dichloromethane was added over a period of 15 minutes keeping the temperature between 10° C. and 15° C. After stirring for 40 minutes and addition of 58.2 g (0.60 mol) N,O-dimethylhydroxylamine hydrochloride a solution of 60.6 g (0.60 mol) triethylamine was added over a period of 20 minutes at 10–15° C. After additional stirring for 30 minutes water was added and the organic layer dried over sodium sulphate. Fractionated distillation in vacuo yielded 131.9 g (81%) B1.

MS: 273 (API+)

Example B2

3-hydroxy-N-methoxy-N-methylbenzamide (B2)

To a solution of 100 g (0.37 mol) B1 in 750 ml tetrahydrofuran 10 g Pd/C (10%) were added and the mixture was hydrogenated at atmospheric pressure for 2 hours. The catalyst was filtered off and the filtrate was evaporated to yield 66.0 g B2 (98%).

MS: 182 (API+), 180 (API–)

Example B3

3-(2-pyridinylmethyloxy)-N-methoxy-N-methylbenzamide (B3)

To a solution of 1.21 g (10.0 mmol) B2, 2.89 g (11.0 mmol) triphenylphosphine and 1.20 g (11.0 mmol) pyridine- 2-methanol in 30 ml dry tetrahydrofuran a solution of 1.92 g (11.0 mmol) diethyl azodicarboxylate in 5 ml dry tetrahydrofuran was added and the mixture was stirred at room temperature for 2 hours. After removal of the solvent and column chromatography on Silica (hexane/ethyl acetate 2:1) 2.81 g B3 were obtained as a light yellow oil (72% yield assuming 30 mol % impurity of triphenylphosphine oxide (measured by NMR)). Due to the problems with the separation of the impurities in this particular example the experiment was repeated with PS-bound triphenylphosphine to give pure B3 in 58% yield.

MS: M=273 (API+)

$^1$H-NMR (400 MHz, CDCl$_3$) δ=3.25 (s, 3H, CH$_3$); 3.45 (s, 3H, OCH$_3$); 5.15 (s, 2H, OCH$_2$); 6.98–7.04 (m, 1H); 7.12–7.28 (m, 4H); 7.40–7.48 (m, 1H); 7.60–7.68 (m, 1H); 8.46–8.56 (m, 1H).

$^{13}$C-NMR (100.6 MHz, CDCl$_3$) δ=34.3 (CH$_3$); 61.5 (OCH$_3$); 71.0 (OCH$_2$); 114.9, 117.6, 121.3, 121.8, 123.2, 129.7, 135.9*, 137.3, 149.6, 157.3*, 158.3* (C$_{arom}$H); 169.9 (C=O).

(*=quatery carbon)

Example B4

3-(3-pyridinylmethyloxy)-N-methoxy-N-methylbenzamide (B4)

An analogous reaction to that described in example B3 but reacting with 3-pyridinylmethanol gave B4 in 81% yield.

MS: M=273 (API+)

$^1$H-NMR (400 MHz, DMSO-D$_6$) δ=3.24 (s, 3H, CH$_3$); 3.53 (s, 3H, OCH$_3$); 5.20 (s, 2H, OCH$_2$); 7.12–7.24 (m, 3H); 7.34–7.48 (m, 2H); 7.84–7.92 (m, 1H); 8.52–8.60 (m, 1H); 8.68–8.72 (m, 1H).

$^{13}$C-NMR (100.6 MHz, DMSO-D$_6$) δ=33.7 (CH$_3$); 61.1 (OCH$_3$); 67.4 (OCH$_2$); 114.1, 117.3, 120.5, 124.0, 129.7, 132.8, 136.1, 136.2, 149.5, 149.6, 157.9 (C$_{arom}$H); 169.0 (C=O).

Example B5

3-(4-pyridinylmethyloxy)-N-methoxy-N-methylbenzamide (B5)

An analogous reaction to that described in example B3 but reacting with 4-pyridinylmethanol gave B5 in 82% yield.

MS: M=273 (API+)

$^1$H-NMR (400 MHz, DMSO-D$_6$) δ=3.24 (s, 3H, CH$_3$); 3.51 (s, 3H, OCH$_3$); 5.24 (s, 2H, OCH$_2$); 7.12–7.22 (m, 3H); 7.34–7.41 (m, 1H); 7.42–7.48 (m, 2H); 8.52–8.64 (m, 2H).

$^{13}$C-NMR (100.6 MHz, DMSO-D$_6$) δ=33.7 (CH$_3$); 61.0 (OCH$_3$); 67.9 (OCH$_2$); 114.1, 117.3, 120.7, 122.1, 129.8, 136.3, 146.4, 150.1, 157.7 (C$_{arom}$H); 169.0 (C=O).

C Synthesis of the "Ethanones"

Example C1

1-(3-(2-pyridinylmethyloxy)phenyl)-2-(2-methylthiopyrimidin-4-yl)-ethanone (C1)

2.1 ml (15 mmol) diisopropylamine were dissolved in 70 ml dry tetrahydrofuran and cooled to −75° C. and 9.4 ml of a solution of n-butyllithium (1.6 M, 15 mmol) were added over a period of 10 minutes. After stirring for 15 minutes at −75° C. a solution of 1.69 g (12 mmol) 2-methylthio-4-methylpyrimidine in 5 ml dry tetrahydrofuran was added within 10 minutes at −75° C. and the mixture was stirred for additional 15 minutes. Then a solution of 2.73 g (7 mmol) B3 (70% purity) in 5 ml dry tetrahydrofuran was added within 10 minutes at −75° C. The mixture was stirred for one hour at −75° C. and then allowed to warm up to room temperature and finally poured on 100 ml ethyl acetate/water (1:1). The aqueous layer was extracted with 50 ml ethyl acetate and the combined organic layers were dried over sodium sulphate. Removal of the solvent in vacuo and column chromatography on Silica (n-heptane/ethyl acetate 3:1) yielded 1.52 g (62%) C1. (keto-enole ratio measured by NMR in CDCl3 at 400 MHz is about 30:70).

MS: M=352 (API+), 350 (API−)

Example C2

1-(3-(3-pyridinylmethyloxy)phenyl)-2-(2-methylthiopyrimidin-4-yl)-ethanone (C2)

An analogous reaction to that described in example C1 but starting with B4 gave C2 in 60% yield

MS: M=352 (API+), 350 (API−)

Example C3

1-(3-(4-pyridinylmethyloxy)phenyl)-2-(2-methylthiopyrimidin-4-yl)-ethanone (C3)

An analogous reaction to that described in example C1 but starting with B5 gave C3 in 55 % yield

MS: M=352 (API+), 350 (API−)

Example C4

1-(3-benzyloxyphenyl)-2-(2-methylthiopyrimidin-4-yl)-ethanone (C4)

An analogous reaction to that described in example C1 but starting with B1 gave C4 in 89 % yield

MS: M=351 (API+), 349 (API−)

D Synthesis of the "Ketoximes"

Example D1

1-(3-(2-pyridinylmethyloxy)phenyl)-2-(2-methylthiopyrimidin-4-yl)-2-hydroxy-iminoethanone (D1)

1.50 g (4.3 mmol) C1 were dissolved in a mixture of 18.6 ml glacial acid, 15.0 ml tetrahydrofuran and 2.0 ml water. After cooling to 5° C. a solution of 353 mg (5.1 mmol) sodium nitrite in 3.5 ml water was added keeping the temperature between 5° C. and 10° C. The cooling was removed and the mixture stirred for 2 hours at room temperature. After removal of the solvent in vacuo 35 ml water and 240 ml ethyl acetate were added. The pH was adjusted to 8 with 3 N NaOH. The phases were separated and the aqueous layer was extracted with 50 ml ethyl acetate. The combined organic layers were dried over sodium sulphate and the solvent was removed in vacuo. Yield: 1.61 g (99%) D1,

MS: M=381 (API+), 379 (API−)

$^1$H-NMR (400 MHz, DMSO-D$_6$) δ=2.17 (s, 3H, SCH3); 5.25 (s, 2H, OCH$_2$); 7.30–7.35 (m, 1H); 7.36–7.42 (m, 3H);

7.47–7.54 (m, 2H); 7.62–7.65 (m, 1H); 7.78–7.85 (m, 1H); 8.52–8.55 (m, 1H); 8.68–8.72 (m, 1H); 12.80 (br, 1H, OH).
$^{13}$C-NMR (100.6 MHz, DMSO-D$_6$) δ=13.6 (SCH$_3$); 70.9 (OCH$_2$); 111.7, 113.8, 121.6, 122.0 122.1, 123.4, 131.0, 136.4*, 137.3, 149.5, 154.0*, 156.5*, 158.7, 158.9*, 159.3*, 171.8*; 193.3*
(C=O). (=quatery carbon)

Example D2

1-(3-(3-pyridinylmethyloxy)phenyl)-2-(2-methylthiopyrimidin-4-yl)-2-hydroxy-iminoethanone (D2)

An analogous reaction to that described in example C1 but starting with C2 gave D2 in 92% yield.
MS: M=381 (API+), 379 (API−)
$^1$H-NMR (400 MHz, DMSO-D$_6$) δ=2.19 (s, 3H, SCH$_3$); 5.23 (s, 2H, OCH$_2$); 7.32–7.46 (m, 4H); 7.46–7.56 (m, 1H); 7.58–7.68 (m, 1H); 7.84–7.92 (m, 1H); 8.50–8.56 (m, 1H); 8.64–8.72 (m, 2H).

Example D3

1-(3-(4-pyridinylmethyloxy)phenyl)-2-(2-methylthiopyrimidin-4-yl)-2-hydroxy-iminoethanone (D3)

An analogous reaction to that described in example C1 but starting with C3 gave D3 in 97% yield.
MS: M=381 (API+), 379 (API−)
$^1$H-NMR (400 MHz, DMSO-D$_6$) δ=2.18 (s, 3H, SCH$_3$); 5.27 (s, 2H, OCH$_2$); 7.36–7.43 (m, 3H); 7.43–7.49 (m, 2H); 7.49–7.55 (m, 1H); 7.61–7.68 (m, 1H); 8.54–8.63 (m, 2H), 8.68–8.74 (m, 1H); 12.78 (s, 1H, OH).

Example D4

1-(3-benzyloxyphenyl)-2-(2-methylthiopyrimidin-4-yl)-2-hydroxyiminoethanone (D4)

An analogous reaction to that described in example C1 but starting with C4 gave D4 in 86% yield.
MS: M=380 (API+), 378 (API−)
$^1$H-NMR (250 MHz, DMSO-D$_6$) δ=2.19 (s, 3H SCH$_3$); 5.17 (s, 2H, OCH$_2$); 7.24–7.53 (m, 9H); 7.59–7.69 (m, 1H); 8.63–8.72 (m, 1H); 12.83 (br, 1H, OH).
$^{13}$C-NMR (62.9 MHz, DMSO-D$_6$) δ=13.6 (SCH$_3$); 69.9 (OCH$_2$); 111.7, 113.7, 121.6, 122.1, 128.1, 128.3, 128.8, 130.9, 136.5*, 136.9*, 154.0*, 158.6, 159.1*, 159.4*, 171.8*; 193.5* (C=O).
(*=quatery carbon)

E Synthesis of the "N-hydroxy Imidazoles"

Example E1

2-(2,6-dichloro-4-[ethoxycarbonylmethoxy]phenyl)-4-(3-(2-pyridinylmethyl-oxy)phenyl)-5-(2-methylthiopyrimidin-4-yl)-N-hydroxy-imidazole (E1)

A mixture of 1.60 g (4.2 mmol) D1, 1.40 g (5.0 mmol) A2 and 3.25 g (42 mmol) ammonium acetate in 40 ml acetic acid was stirred at 105° C. for 3.5 hours. The solvent was distilled off and the residue was partitionated between 40 ml ice water and 60 ml ethyl acetate and adjusted to pH 8 with conc. aqueous ammonia. The aqueous layer was extracted with ethyl acetate and the combined organic layers were dried over MgSO$_4$ and evaporated to dryness to yield 3.60 g of a light brown, slowly solidifying oil which was used for the next step (example F1) without further purification.
MS: M=638 (API+), 636 (API−)

Example E2

2-(2,6-dichloro-4-[ethoxycarbonylmethoxy]phenyl)-4-(3-(3-pyridinylmethyl-oxy)phenyl)-5-(2-methylthiopyrimidin-4-yl)-N-hydroxy-imidazole (E2)

An analogous reaction to that described in example E1 but starting with D2 yielded E2 as an orange oil.
MS: M=638 (API+), 636 (API−)

Example E3

2-(2,6-dichloro-4-[ethoxycarbonylmethoxy]phenyl)-4-(3-(4-pyridinylmethyl-oxy)phenyl)-5-(2-methylthiopyrimidin-4-yl)-N-hydroxy-imidazole (E3)

An analogous reaction to that described in example E1 but starting with D3 yielded E3 as a yellow solid.
MS: M=638 (API+), 636 (API−)

Example E4

2-(3,5-dichloropyridin-4-yl)-4-(3-benzyloxyphenyl)-5-(2-methylthiopyrimidin-4-yl)-N-hydroxy-imidazole (E4)

An analogous reaction to that described in example E1 but starting with D4 and 3,5-dichloropyridine-4-carboxaldehyde (J. Med. Chem. 44 (2001) 997) yielded E4 as a orange solid.
MS: M=536 (API+), 534 (API−)

F Synthesis of the "N—H Imidazoles"

Example F1

2-(2,6-dichloro-4-[methoxycarbonylmethoxy]phenyl)-4-(3-(2-pyridinylmethyl-oxy)phenyl)-5-(2-methylthiopyrimidin-4-yl)-N—H-imidazole (F1)

A mixture of 3.59 g (4.2 mmol) E1, 1.41 g (8.4 mmol) methyl bromoacetate and 2.85 g (28 mmol) triethylamine in 80 ml methanol was stirred overnight at 60° C. After removal of the solvent in vacuo column chromatography on silica (ethyl acetate/iso-hexane 3:1) returned 2.08 g (81%) pure F1 (transesterification in methanol).
MS: M=608 (API+), 606 (API−)

Example F2

2-(2,6-dichloro-4-[methoxycarbonylmethoxy]phenyl)-4-(3-(3-pyridinylmethyl-oxy)phenyl)-5-(2-methylthiopyrimidin-4-yl)-N—H-imidazole (F2)

An analogous reaction to that described in example F1 but starting with E2 yielded 65% F2.
MS: M=608 (API+), 606 (API−)

Example F3

2-(2,6-dichloro-4-[methoxycarbonylmethoxy]phenyl)-4-(3-(4-pyridinylmethyl-oxy)phenyl)-5-(2-methylthiopyrimidin-4-yl)-N—H-imidazole (F3)

An analogous reaction to that described in example F1 but starting with E3 yielded 66% F3.
MS: M=608 (API+), 606 (API−)

Example F4

2-(2,6-dichloro-4-[2-hydroxyethoxy]phenyl)-4-(3-(2-pyridinylmethyloxy)phenyl)-5-(2-methylthiopyrimidin-4-yl)-N—H-imidazole (F4)

To a solution of 2.07 g (3.3 mmol) F1 in 50 ml dry THF under nitrogen LiAlH$_4$ (1M in THF) was added at 0° C. until F1 could no longer be detected by HPLC. After hydrolysis with 0.5 ml water and removal of the solvent the residue was purified by column chromatography on silica (ethyl acetate/methanol 9:1) to yield 93% F4.
MS: M=580 (API+), 578 (API−)

Example F5

2-(2,6-dichloro-4-[2-hydroxyethoxy]phenyl)-4-(3-(3-pyridinylmethyloxy)phenyl)-5-(2-methylthiopyrimidin-4-yl)-N—H-imidazole (F5)

An analogous reaction to that described in example F4 but starting with F2 yielded 64% F5.
MS: M=580 (API+), 578 (API−)

Example F6

2-(2,6-dichloro-4-[2-hydroxyethoxy]phenyl)-4-(3-(4-pyridinylmethyloxy)phenyl)-5-(2-methylthiopyrimidin-4-yl)-N—H-imidazole (F6)

An analogous reaction to that described in example F4 but starting with F3 yielded 69% F6.
MS: M=580 (API+), 578 (API−)

Example F7

2-(3,5-dichloropyridin-4-yl)-4-(3-benzyloxyphenyl)-5-(2-methylthiopyrimidin-4-yl)-N—H-imidazole (F7)

An analogous reaction to that described in example F1 but starting with E4 yielded 66% F7.
MS: M=520 (API+), 518 (API−)

G Synthesis of the "N—H Imidazoles Sulfines" and "N—H Imidazoles Sulfones"

Example G1

2-(2,6-dichloro-4-[2-hydroxyethoxy]phenyl)-4-(3-(2-pyridinylmethyloxy)phenyl)-5-(2-methanesulfinylpyrimidin-4-yl)-N—H-imidazole (G1)

To a solution of 1.20 g (2.1 mmol) F4 in 300 ml ethyl acetate and 50 ml dichloromethane a solution of 0.70 g (3.1 mmol) m-chloroperoxybenzoic acid in 20 ml ethyl acetate was added over 10 minutes at −40° C. After 1 hour at this temperature the mixture was allowed to warm up to room temperature and stirred overnight. The mixture was washed (saturated aqueous NaHCO$_3$/saturated aqueous Na$_2$CO$_3$ 1:1) dried over MgSO$_4$ and evaporated to dryness to yield 1.21 g crude G1 which was used without further purification.
MS: M=596 (API+), 594 (API−)

Example G2

2-(2,6-dichloro-4-[2-hydroxyethoxy]phenyl)-4-(3-(3-pyridinylmethyloxy)phenyl)-5-(2-methanesulfinylpyrimidin-4-yl)-N—H-imidazole (G2)

An analogous reaction to that described in example G1 but starting with F5 gave G2.
MS: M=596 (API+), 594 (API−)

Example G3

2-(2,6-dichloro-4-[2-hydroxyethoxy]phenyl)-4-(3-(4-pyridinylmethyloxy)phenyl)-5-(2-methanesulfinylpyrimidin-4-yl)-N—H-imidazole (G3)

An analogous reaction to that described in example G1 but starting with F6 gave G3.
MS: M=596 (API+), 594 (API−)

Example G4

2-(3,5-dichloropyridin-4-yl)-4-(3-benzyloxyphenyl)-5-(2-methanesulfanyl-pyrimidin-4-yl)-N—H-imidazole (G4)

2.38 g (4.6 mmol) F7 were suspended in 200 ml methanol and a solution of 5.62 g (9.1 mmol) Oxone™ was added at room temperature within 20 minutes. After stirring at room temperature overnight the methanol was removed in vacuo and the residue was taken up with ethyl acetate. The organic layer was washed with aqueous NaHCO$_3$, dried over Na$_2$SO$_4$ and evaporated to dryness. The crude G4 (47%) was used without further purification.
MS: M=552 (API+), 550 (API−)

H Synthesis of the "N—H Imidazoles Aminopyrimidines"

Example H1

2-(2,6-dichloro-4-[2-hydroxyethoxy]phenyl)-4-(3-(2-pyridinylmethyloxy)phenyl)-5-(2-[3-hydroxypropylamino]pyrimidin-4-yl)-N-1H-imidazole (H1)

1.21 g (2.0 mmol) G1 and 3.1 g (40.6 mmol) 3-amino-1-propanol were heated to 110° C. for 60 minutes. Purification by preparative scale HPLC/MS on RP 18 (methanol-water-gradient) yielded 510 mg (42%) H1.
MS: M=607 (API+), 605 (API−)

Example H2

2-(2,6-dichloro-4-[2-hydroxyethoxy]phenyl)-4-(3-(3-pyridinylmethyloxy)phenyl)-5-(2-[3-hydroxypropylamino]pyrimidin-4-yl)-N-1H-imidazole (H2)

An analogous reaction to that described in example H1 but starting with G2 yielded 50% H2.
MS: M=607 (API+), 605 (API−)

Example H3

2-(2,6-dichloro-4-[2-hydroxyethoxy]phenyl)-4-(3-(4-pyridinylmethyloxy)phenyl)-5-(2-[3-hydroxypropylamino]pyrimidin-4-yl)-N-1H-imidazole (H3)

An analogous reaction to that described in example H1 but starting with G3 yielded 32% H3.
MS: M=607 (API+), 605 (API−)

Example H4

2-(3,5-dichloropyridin-4-yl)-4-(3-benzyloxyphenyl)-5-(2-[3-hydroxypropyl-amino]pyrimidin-4-yl)-N-1H-imidazole (H4)

An analogous reaction to that described in example H1 but starting with G4 yielded 68% H4.
MS: M=547 (API+), 545 (API−)

Example I

C-met Autoactivation Kinase Assay (AKA)

Assay Principle

C-met is a typical tyrosine kinase which is involved in metastasis, proliferation/apoptosis and angiogenesis of tumors. The assay is an ELISA type assay measuring the phosphorylation of c-met using a phospho-tyrosine specific antibody.

Cell lysate of human colon adenocarcinoma HT29 known for its high content of c-met is bound to the wells of a microtiterplate (MTP) via an anti-hHGF receptor antibody (anti-hHGFR). ATP-phosphorylation of c-met is detected in presence or absence of the test compounds by using a phospho-tyrosine mouse IgG and a POD labeled goat anti-mouse IgG detection system. Using the classical POD substrate TMB, an absorption at 450 nm/620 nm is used to calculate enzymatic activity.

Materials:
Plates: 96-well polystyrene plates (NUNC) streptavidin-coated microtiter plates Cell line/Lysate: HT29 (ATCC HTB-38), human colon adenocarcinoma (confluence: 2.5× $10^5$ cells/cm$^2$) are washed with PBS and incubated with Lysis buffer for 10 min on ice. Supernatent is collected and diluted with TBS. Lysate is shockfrozen in liquid nitrogen and stored at −80° C.)

Reagents (all working solutions are kept at 4° C., unless stated otherwise):
anti-hHGFR detection stock solution: 50 µg/ml (R&D Systems, Cat.No. BAF 358) antibody final conc.: 1 µg/ml
p-Tyr (PY99) mouse stock solution: 200 µg/ml (Santa Cruz Biotechnology, monoclonal IgG2b Cat.No. SC-7020) final conc.: 0.2 µg/ml
goat-anti-mouse IgG: 2 ml (BIO RAD, Cat.No. 170–6516) (H+L)-HRP Conjugate; final conc.: 1:2000
Blocking Reagent: Roche Diagnostics GmbH, Cat.No.1 112589 for ELISA diluted 1:10 in TBS
ATP: Adenosine-5'-triphosphate, stock solution 10 mM, stock solution 10 mM (Roche Diagnostics GmbH, Cat.No. 127531) final conc.: 40 µM
TBS: Tris-buffered saline, 50 mM TRIS pH 7.5 (Roche Diagnostics GmbH, Cat.No. 708976), 150 mM NaCl (SIGMA, Cat.No. S-3014)
Wash buffer TBS-T: Tris-buffered saline, 50 mM TRIS pH 7.5 150 mM NaCl, containing 0.5% Tween20
Kinase buffer: Tris-buffered saline, 50 mM TRIS pH 7.5, 100 mM NaCl, 60 mM MgCl$_2$ (SIGMA Chemical Company, Cat.No. M-1028)
Lysis buffer: 50 mM TRIS pH 7.5 containing 1% Nonidet P40 (Roche Diagnostics GmbH, Cat.No.1754599) 0.5 % Deoxycholic acid (SIGMA Chemical Company, Cat.No. D-6750) final conc.: 1 mM 1 mM PMSF stock solution 70 mM (Roche Diagnostics GmbH, Cat.No.837091 40 µl/ml Complete (Roche Diagnostics GmbH, Cat.No. 1836145) Final conc.: 40 µ/ml
TMB: Tetramethylbenzidine (Intergen Company, Cat.No. 91000)
Samples: 10 mM in DMSO (stored at −20° C.), thawed at room temperature Procedure:
Add 50 µl of anti-hHGFR detection antibody in blocking reagent to assay plate (final conc. 1 µg/ml), incubate assay plate for 60 min at room temperature on an MTP shaker.
Remove anti-hHGFR detection antibody solution from assay plate.
Add 250 µl blocking reagent per well to assay plate, incubate assay plate for 20 h, at 4° C.
Remove blocking reagent from assay plate.
Add 50 µl of HT29 lysate, incubate assay plate for 180 min, at 4° C. on an MTP shaker.
Wash assay plate with 2×200 µl TBS buffer per well.
Add 40 µl of 0.2% DMSO in kinase buffer to assay plate.
Add 40 µl sample solution (dissolved in kinase buffer—final conc. 22.5 µM).
Dissolve samples (1:3 ratio) in MTP.
Add 10 µl ATP dissolved in kinase buffer (200 µM) to samples (final conc. 40 µM ATP).
Positive control: add 40 µl kinase buffer plus 10 µl 200 µM ATP. Negative control: add 40 µl kinase buffer plus 10 µl kinase buffer without ATP. Incubate assay plate for 60 min at room temperature on an MTP shaker.
Wash assay plate with 2×200 µl TBS buffer and 2×200 µl blocking reagent per well.
Add 50 µl of P-Tyr (PY99) mouse monoclonal IgG$_{2b}$ in blocking reagent (final conc. 200 ng/ml) to assay plate, incubate assay plate over night at 4° C. on an MTP shaker.
Wash assay plate with 2×200 µl TBS buffer and 2×200 µl blocking reagent per well.
Add 50 µl of goat anti-mouse IgG (H+L)-HRP conjugate in blocking reagent (1:2000 ratio), incubate assay plate for 60 min at room temperature on an MTP shaker.
Wash assay plate with 6×2001 µl TBS-T buffer per well.
Add 50 µl TMB solution, incubate for 30 min at room temperature on an MTP shaker, add 25 µl 1 M H$_2$SO$_4$.
Measure optical density (E) at 450 nm /620 nm.
Calculate % inhibition as:

$$1-[(E_{sample}-E_{negative\ control})/(E_{positive\ control}-E_{negative\ control})\times 100]$$

Agents of the invention typically have IC$_{50}$ values for kinase inhibition in the range from about 1 nM to about 100 nM when tested in the above assay:

| Example | IC$_{50}$ C-met [nM] |
| --- | --- |
| H4 | 23 |
| H1 | 22 |
| H2 | 32 |
| H3 | 54 |

Example K

Tablet Formulation (Wet Granulation)

| Item | Ingredients | mg/tablet | | | |
|---|---|---|---|---|---|
| 1. | Compound of formula (I) | 5 | 25 | 100 | 500 |
| 2. | Lactose Anhydrous DTG | 125 | 105 | 30 | 150 |
| 3. | Sta-Rx 1500 | 6 | 6 | 6 | 30 |
| 4. | Microcrystalline Cellulose | 30 | 30 | 30 | 150 |
| 5. | Magnesium Stearate | 1 | 1 | 1 | 1 |
| | Total | 167 | 167 | 167 | 831 |

Manufacturing Procedure
1. Mix items 1, 2, 3 and 4 and granulate with purified water.
2. Dry the granules at 50° C.
3. Pass the granules through suitable milling equipment.
4. Add item 5 and mix for three minutes; compress on a suitable press.

Example L

Capsule Formulation

| Item | Ingredients | mg/capsule | | | |
|---|---|---|---|---|---|
| 1. | Compound of formula (I) | 5 | 25 | 100 | 500 |
| 2. | Hydrous Lactose | 159 | 123 | 148 | — |
| 3. | Corn Starch | 25 | 35 | 40 | 70 |
| 4. | Talc | 10 | 15 | 10 | 25 |
| 5. | Magnesium Stearate | 1 | 2 | 2 | 5 |
| | Total | 200 | 200 | 300 | 600 |

Manufacturing Procedure
1. Mix items 1, 2 and 3 in a suitable mixer for 30 minutes.
2. Add items 4 and 5 and mix for 3 minutes.
3. Fill into a suitable capsule.

LIST OF REFERENCES

Abounader, R., et al., J. Natl. Cancer Inst. 91 (1999) 1548–1556
Ansel et. al., Pharmaceutical Dosage Forms and Drug Delivery Systems, 6th ed., (1995), pp. 196 and 1456–1457
Baldwin, J. J., et al., J. Med. Chem. 22 (1979) 687–693
Blume-Jensen, P., and Hunter, T., Nature 411 (2001) 355–365
Gust, R., and Schoenenberg, H., Eur. J. Med. Chem. 28 (1993) 103–115
Herynk, M. H., and Radinsky, R., In Vivo 14 (2000) 587–596
Hubbard, S. R., et al., J. Biol. Chem. 273 (1998) 11987–11990
Jiang, W., et al., Crit. Rev. Oncol. Hematol. 29 (1999) 209–248 J. Med. Chem. 44 (2001) 997
Laterra, J., et al., Lab. Invest. 76 (1997) 565–577
Longati, P., et al., Curr. Drug Targets 2 (2001) 41–55
Maulik, G., et al., Cytokine Growth Factor Rev. 13 (2002) 41–59
Parr, C., and Jiang, W. G., Histol. Histopathol. 16 (2001) 251–268
Somei, M., and Tsuchiya, M., Chem. Pharm. Bull. 29 (1981) 3145–3157
Tomioka, D., Cancer Res. 61 (2001) 7518–7524
Wang, R., et al., J. Cell Biol. 153 (2001) 1023–1033
WO 01/44154
WO 96/18626
Zwick, E., et al., Trends Mol. Med. 8 (2002) 17–23

What is claimed:

1. Compounds of general formula (I):

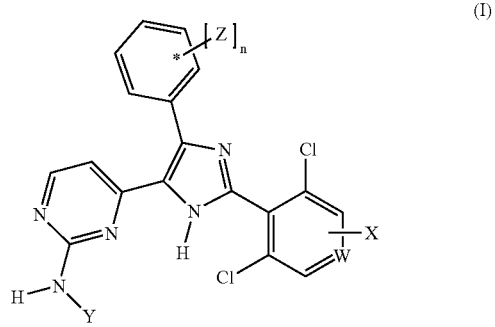

wherein
W —is N=;
X is hydrogen;
Y is hydrogen or a group $A^2$—R;
$A^2$ is $C_1$–$C_5$-alkylene, which maybe optionally substituted by $C_1$–C6-alkyl, phenyl or by hydroxy;
R is selected from the group consisting of hydroxy; linear or branched $C_1$–$C_6$-alkoxy; amino; dimethylamino; diethylamino; t-butyloxycarbonylamino; carboxyl; $C_1$ –$C_6$-alkoxycarbonyl; triazolyl; cyano; piperidino; 1 -pyrrolidinyl; morpholino; 4-methylpiperazin-1-yl; O—$A^1$—$NR^3R^4$; S —$A^1$—$NR^3R^4$; 4-carboxyphenyl; furan-3 -yl; thiophen-2-yl; and 3-methylthiophen-2-yl;
n is 1 or 2; and
Z is one or two substituents independently selected from the group consisting of halogen; hydroxy; allyloxy; methyl; $C_1$–$C_3$-alkoxy, which are optionally substituted with pyridinyl; methoxymethoxy; (2-methoxyethoxy) methyloxy; methylthio; ethoxymethoxy; methylendioxy; ethynyl; trimethylsilylethynyl; benzyloxy which is optionally substituted by halogen; methoxy; cyano; nitro; methylendioxy; carboxy and ethoxy;
or alternatively;
W is —CH=;
X is selected from the group consisting of hydrogen; $OR^1$; $SR^2$; (SO)$R^2$; (SO$_2$)$R^2$; CH$_2$—S—CH$_2$—C(O)$_2$—CH$_2$—CH$_3$; CH$_2$—S—(CH$_2$)$_2$—OH; and a group $A^1$-Q;
$A^1$ represents a $C_1$–$C_3$-alkylene group;
Q is selected from the group consisting of $OR^1$; $SR^2$; $SOR^2$; $SO_2R^2$; $NR^3R^4$; $NHCH_2CH_2NR^3R^4$ and halogen;
$R^1$ is selected from the group consisting of hydrogen; $C_1$–$C_3$-alkyl; allyl; dimethylphosphonylmethyl; 2,3-epoxy-1-propyl; (R)-2,3-dihydroxy-1-propyl; (S)-2,3-dihydroxy-1-propyl; 1,3-dihydroxy-2-propyl; 3-hydroxy-2-hydroxymethyl-1-propyl; 2- methoxyethoxymethyl; 2,2-dimethyl-1,3-dioxolan-4-ylmethyl; and a group $A^1$-$Q^1$;
$Q^1$ is selected from the group consisting of $C_1$–$C_2$-alkoxy; cyano; carboxyl; $C_1$–$C_6$- alkoxycarbonyl; carboxamide; —CO—NR$^3$R$^4$; C$_1$–C$_6$-alkylsulfanyl; C$_1$–C$_6$-alkylsulfenyl; and C$_1$–C$_6$-alkylsulfonyl; except if A$^1$ represents a[n] 1,2-ethylen- or 1,3-propylen group, then Q$^1$ is hydroxy or NR$^3$R$^4$;

R$^2$ is selected from the group consisting of C$_1$–C$_6$-alkyl; dimethylphosphonylmethyl; 2,3-epoxy-1-propyl; 2,3-dihydroxy-1-propyl; 2,2-dimethyl-1,3-dioxolan-4-ylmethyl; and A$^1$–Q$^1$;

R$^3$ and R$^4$ are independently selected from the group consisting of hydrogen and C$_1$–C$_6$-alkyl; or alternatively R$^3$ and R$^4$ together form a 5 to 7 membered, saturated or unsaturated ring, optionally substituted by a methyl group and containing one or two heteroatoms, independently selected from the group consisting of N and O;

Y is hydrogen or a group A$^2$-R;

A$^2$ is C$_1$–C$_5$-alkylene, which may be optionally substituted by C$_1$–C$_6$-alkyl, phenyl or by hydroxy;

R is selected from the group consisting of hydroxy; linear or branched C$_1$–C$_6$- alkoxy; amino; dimethylamino; diethylamino; t-butyloxycarbonylamino; carboxyl; C$_1$–C$_6$- alkoxycarbonyl; triazolyl; cyano; piperidino; 1-pyrrolidinyl; morpholino; 4- methylpiperazin-1-yl; O—A$^1$—NR$^3$R$^4$; S—A$^1$—NR$^3$R$^4$; 4-carboxyphenyl; furan-3-yl; thiophen- 2-yl; and 3-methylthiophen-2-yl;

n is 1 or 2; and

Z represents C$_1$–C$_3$-alkoxy, substituted with pyridinyl if n is 1; or alternatively if n is 2, one substituent is C$_1$–C$_3$-alkoxy, substituted with pyridinyl, and the second substituent is independently selected from the gorup consisting of halogen; hydroxy; allyloxy; methyl; C$_1$–C$_3$-alkoxy; methoxymethoxy; (2-methoxyethoxy) methyloxy; methylthio; ethoxymethoxy; methylendioxy; ethynyl; and trimethylsilylethynyl;

or pharmaceutically acceptable salts thereof.

2. The compounds of claim 1, wherein:

W is —N═;

X is hydrogen;

Y is selected from the group consisting of 2-hydroxyethyl; 3-hydroxypropyl; 2-methoxyethyl; 3-methoxypropyl; (R)-2,3-dihydroxy-1-propyl; (S)-2,3-dihydroxy-1-propyl; (R) -3-hydroxybutyl; (S)-3-hydroxybutyl; 3-Hydroxy-2,2-dimethylpropyl; 2-morpholinoethyl; 3-morpholinopropyl; 2-(4-methylpiperazin-1-yl)ethyl; 3-hydroxy-1-phenylpropyl; 2-aminoethyl; 3-aminopropyl; 4-aminobutyl; 2-(N,N-dimethylamino)ethyl; 3-(N,N-dimethylamino)propyl; 3-(pyrrolidin-1-yl)propyl; CH$_2$COOH; (CH$_2$)$_2$COOH; (CH$_2$)$_3$COOH; CH(C$_2$H$_5$)COOH; (CH$_2$)$_2$—O—(CH$_2$)$_2$—N(CH$_3$)$_2$; (CH$_2$)$_2$—O—(CH$_2$)$_2$—NH$_2$; (CH$_2$)$_2$—S —(CH$_2$)$_2$—N(CH$_3$)$_2$; (CH$_2$)$_2$—S—(CH$_2$)$_3$—N(CH$_3$)$_2$; (CH$_2$)$_3$—S—(CH$_2$)$_2$—N(CH$_3$)$_2$; and (CH$_2$)$_3$—S—(CH$_2$)$_3$—N(CH$_3$)$_2$;

n is1 and Z is selected from the group consisting of 3-chloro; 4-chloro; 3-bromo; 3-iodo; 3-ethynyl; 3-methoxymethoxy; 3-benzyloxy which is optionally substituted by halogen; methoxy; cyano; nitro; methylendioxy; carboxy; and ethoxy.

3. The compounds of claim 1, wherein:

W is—N═;

X is hydrogen;

Y is selected from the group consisting of 2-hydroxyethyl; 3-hydroxypropyl; (R)-2,3-dihydroxy-1-propyl; (S)-2,3-dihydroxy-1-propyl; 2-morpholinoethyl; 3-morpholino-propyl; 2-(4-methylpiperazin-1-yl) ethyl; 2-aminoethyl; 3-aminopropyl; 2-(N,N-dimethylamino) ethyl; 3-(N,N-dimethylamino)propyl; and 3-(pyrrolidin-1-yl)propyl;

n is 1 ; and

Z is selected from the group consisting of 3-chloro; 4-chloro; 3-bromo; 3-iodo; 3-ethynyl; 3-methoxymethoxy; 3-benzyloxy which is optionally substituted by halogen; methoxy; and cyano.

4. A compound of claim 3 which is:

2-(3,5-dichloropyridin-4-yl)-4-(3-benzyloxyphenyl)-5-(2-[3-hydroxypropyl-amino]pyrimidin-4-yl)-N-1H-imidazole.

5. The compounds of claim 1, wherein:

W is —CH═;

X is selected from the group consisting of hydrogen; OR$^1$; SR$^2$; (SO)R$^2$; (SO$_2$)R$^2$;CH$_2$—S—CH$_2$—C(O)$_2$—CH$_2$—CH$_3$; CH$_2$—S—(CHD$_2$—OH; and a group A$^1$—Q;

A$^1$ represents a C$_1$–C$_3$-alkylene group;

Q is selected from the group consisting of OR$^1$; SR$^2$; SOR$^2$; SO$_2$R$^2$; NR$^3$R$^4$;

NHCH$_2$CH$_2$NR$^3$R$^4$; and halogen;

R$^1$ is selected from the group consisting of hydrogen; C$_1$–C$_3$-alkyl; allyl; dimethylphosphonylmethyl; 2,3-epoxy-1-propyl; (R)-2,3-dihydroxy-1-propyl; (S)-2,3-dihydroxy-1-propyl; 1,3-dihydroxy-2-propyl; 3-hydroxy-2-hydroxymethyl-1-propyl; 2-methoxy - ethoxymethyl; 2,2-dimethyl-1,3-dioxolan-4-ylmethyl; and a group A$^1$—Q$^1$;

Q$^1$ is selected from the group consisting of C$_1$–C$_2$-alkoxy; cyano; carboxyl; C$_1$–C$_6$-alkoxycarbonyl; carboxamide; —CO—NR$^3$R$^4$; C$_1$–C$_6$-alkylsulfanyl; C$_1$–C$_6$-alkylsulfenyl; and C$_1$–C$_6$alkylsulfonyl; except if A$^1$ represents a 1,2-ethylen- or 1,3-propylen group, then Q$^1$ is hydroxy or NR$^3$R$^4$;

R$^2$ is selected from the group consisting of C$_1$C$_6$-alkyl; dimethylphosphonylmethyl; 2,3-epoxy-1-propyl; 2,3-dihydroxy-1-propyl; 2,2-dimethyl-1,3-dioxolan-4-ylmethyl; and A$^1$—Q$^1$; R$^3$and R$^4$ are independently selected from the group consisting of hydrogen and C$_1$–C$_6$-alkyl; or alternatively R$^3$ and R$^4$ together form a 5 to 7 membered, saturated or unsaturated ring, optionally substituted by a methyl group and containing one or two heteroatoms, independently selected from the group consisting of N and O;

Y is hydrogen or a group A$^2$-R;

A$^2$ is C$_1$–C5-alkylene, which may be optionally substituted by C$_1$–C$_6$-alkyl, phenyl or by hydroxy;

R is selected from the group consisting of hydroxy; linear or branched C$_1$–C$_6$-alkoxy; amino; dimethylamino; diethylamino; t-butyloxycarbonylamino; carboxyl; C$_1$–C$_6$-alkoxycarbonyl; triazolyl; cyano; piperidino; 1-pyrrolidinyl; morpholino; 4-methylpiperazin-1-yl; O—A$^1$—NR$^3$R$^4$; S—A$^1$—NR$^3$R$^4$; 4-carboxyphenyl; furan-3-yl; thiophen-2-yl; and 3-methylthiophen-2-yl;

n is 1; and

Z represents a C$_1$–C3-alkoxy, which is substituted with pyridinyl.

6. The compounds of claim 1, wherein:

W is—CH═;

X is selected from the group consisting of hydrogen; OR$^1$; SR$^2$; (SO)R$^2$; (SO$_2$)R$^2$; CH$_2$—S—CH$_2$—C(O)$_2$—CH$_2$—CH$_3$; CH$_2$—S—(CH$_2$)$_2$—OH; and a group A$^1$—Q;

A$_1$ represents a C$_1$–C$_3$-alkylene group;

Q is selected from the group consisting of OR$^1$; SR$^2$; SOR$^2$; SO$_2$R$^2$; NR$^3$R$^4$; NHCH$_2$CH$_2$NR$^3$R$^4$; and halogen;

R$^1$ is selected from the group consisting of hydrogen; C$_1$–C$_3$-alkyl; allyl; dimethylphosphonylmethyl; 2,3- epoxy-1-propyl; (R)-2,3-dihydroxy-1-propyl; (S)-2,3-dihydroxy-1-propyl; 1,3-dihydroxy-2propyl; 3-hydroxy-2hydroxymethyl-1-propyl; 2-methoxyethoxymethyl; 2,2-dimethyl-1,3-dioxolan-4-ylmethyl; and a group $A^1$—$Q^1$;

$Q^1$ represents $C_1$–$C_2$-alkoxy; cyano; carboxyl; $C_1$–$C_6$-alkoxycarbonyl; carboxamide; —CO—$NR^3R^4$; $C_1$–$C_6$-alkylsulfanyl; $C_1$–$C_6$—alkylsulfenyl; or $C_1$–$C_6$-alkylsulfonyl; except if $A^1$ represents a 1,2-ethylen- or 1,3-propylen group, then $Q^1$ is hydroxy or $NR^3R^4$;

$R^2$ is selected from the group consisting of $C_1$–$C_6$-alkyl; dimethylphosphonylmethyl; 2,3-epoxy-1-propyl; 2,3-dihydroxy-1-propyl; 2,2-dimethyl-1,3-dioxolan-4-ylmethyl; and $A^1$—$Q^1$;

$R^3$ and $R^4$ are independently selected from the group consisting of hydrogen and $C_1$–$C_6$-alkyl; or alternatively $R^3$ and $R^4$ together form a 5 to 7 membered, saturated or unsaturated ring, optionally substituted by a methyl group and containing one or two heteroatoms, independently selected from the group consisting of N and O;

Y is 3-hydroxypropyl;

n is 1; and

Z is pyridin-2-ylmethoxy; pyridin-3-ylmethoxy or pyridin-4-ylmethoxy.

7. A compound of claim 6 which is selected from the group consisting of:
2(2,6-dichloro-4-[2hydroxyethoxy]phenyl)-4-(3-(4-pyridinylmethyloxy)-phenyl)-5(2-[3-hydroxypropylamino]pyrimidin-4-yl)-N-1H-imidazole; 2(2,6-dichloro-4[2-hydroxyethoxy]phenyl)-4(3 (3pyridinylmethyloxy)-phenyl) -5(2-[3-hydroxypropylamino]pyrimidin-4-yl)-N-1H-imidazole; and
2(2,6-dichloro-4-[2-hydroxyethoxy]phenyl)-4-(3-(3-pyridinylmethyloxy)-phenyl)-5-(2-[3-hydroxypropylamino]pyrimidin-4yl)-N-1H-imidazole.

8. A process for the manufacture of a compound of formula:

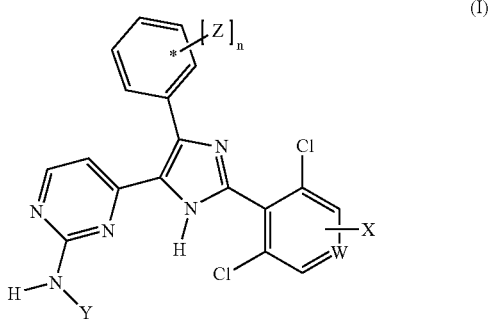

(I)

wherein:

W is —N=;

X is hydrogen;

Y is hydrogen or a group $A^2$—R;

$A^2$ is $C_1$–$C_5$-alkylene, which may be optionally substituted by $C_1$–$C_6$-alkyl, phenyl or by hydroxy;

R is selected from the group consisting of hydroxy; linear or branched $C_1$–$C_6$-alkoxy; amino; dimethylamino; diethylamino; t-butyloxycarbonylamino; carboxyl; $C_1$–$C_6$-alkoxycarbonyl; triazolyl; cyano; piperidino; 1—pyrrolidinyl; morpholino; 4-methylpiperazin-1-yl; O—$A^1$—$NR^3R^4$; S—$A^1$—$NR^3R^4$; 4-carboxyphenyl; furan-3yl; thiophen-2-yl ; and 3-methylthiophen-2yl;

n is 1 or 2; and

Z is one or two substituents independently selected from the group consisting of halogen; hydroxy; allyloxy; methyl; $C_1$–$C_3$-alkoxy, which are optionally substituted with pyridinyl; methoxymethoxy; (2 -methoxyethoxy) methyloxy; methylthio; ethoxymethoxy; methylendioxy; ethynyl; trimethylsilylethynyl; benzyloxy which is optionally substituted by halogen; methoxy; cyano; nitro; methylendioxy; carboxy and ethoxy;

or alternatively:

W is —CH=;

X is selected from the group consisting of hydrogen; $OR^1$; $SR^2$; $(SO)R^2$; $(SO_2)R^2$; $CH_2$—S—$CH_2$—$C(O)_2$—$CH_2$—$CH_3$; $CH_2$—S—$(CH_2)_2$—OH; and a group $A^1$—Q;

$A^1$ represents a $C_1$–C3-alkylene group;

Q is selected from the group consisting of $OR^1$; $SR^2$; $SOR^2$; $SO_2R^2$; $NR^3R^4$; $NHCH_2CH_2NR^3R^4$ and halogen;

$R^1$ is selected from the group consisting of hydrogen; $C_1$–$C_3$-alkyl; allyl; dimethylphosphonylmethyl; 2,3-epoxy-1-propyl; (R)-2,3-dihydroxy-1-propyl; (S)-2,3-dihydroxy-1-propyl; 1,3-dihydroxy-2propyl; 3-hydroxy-2-hydroxymethyl-1-propyl; 2methoxyethoxymethyl; 2,2-dimethyl-1,3-dioxolan-4-ylmethyl; and a group $A^1$—$Q^1$;

$Q^1$ is selected from the group consisting of $C_1$–$C_2$-alkoxy; cyano; carboxyl; $C_1$–$C_6$-alkoxycarbonyl; carboxamide; —CO—$NR^3R^4$; $C_1$–$C_6$-alkylsulfanyl; $C_1$–$C_6$-alkylsulfenyl; and $C_1$–$C_6$-alkylsulfonyl; except if $A^1$ represents a 1,2-ethylen- or 1,3-propylen group, then $Q^1$ is hydroxy or $NR^3R^4$;

$R^2$ is selected from the group consisting of $C_1$–$C_6$-alkyl; dimethylphosphonylmethyl; 2,3-epoxy-1-propyl; 2,3-dihydroxy-1-propyl; 2,2-dimethyl-1,3-dioxolan-4-ylmethyl; and $A^1$–$Q^1$;

$R^3$ and $R^4$ are independently selected from the group consisting of hydrogen and $C_1$–$C_6$-alkyl; or alternatively $R^3$ and $R^4$ together form a 5 to 7 membered, saturated or unsaturated ring, optionally substituted by a methyl group and containing one or two heteroatoms, independently selected from the group consisting of N and O;

Y is hydrogen or a group $A^2$—R;

$A^2$ is $C_1$–$C_5$-alkylene, which may be optionally substituted by $C_1$–$C_6$-alkyl, phenyl or by hydroxy;

R is selected from the group consisting of hydroxy; linear or branched $C_1$–$C_6$-alkoxy; amino; dimethylamino; diethylamino; t-butyloxycarbonylamino; carboxyl; $C_1$–$C_6$-alkoxycarbonyl; triazolyl; cyano; piperidino; 1pyrrolidinyl; morpholino; 4-methylpiperazin-1-yl; O—$A^1$—$NR^3R^4$; S—$A^1$—$NR^3R^4$; 4-carboxyphenyl; furan-3-yl; thiophen-2-yl; and 3-methylthiophen-2-yl;

n is 1 or 2; and

Z represents $C_1$–$C_3$-alkoxy, substituted with pyridinyl if n is 1; or alternatively if n is 2, one substituent is $C_1$–$C_3$-alkoxy, substituted with pyridinyl, and the second substituent is independently selected from the group consisting of halogen; hydroxy; allyloxy; methyl; $C_1$–$C_3$-alkoxy; methoxymethoxy; (2-methoxyethoxy) methyloxy; methylthio; ethoxymethoxy; methylendioxy; ethynyl; and trimethylsilylethynyl;

or pharmaceutically acceptable salts thereof;

which comprises reacting a compound of the formula

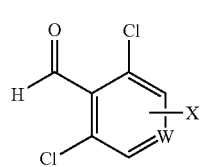
(II)

with a compound of the general formula (III)

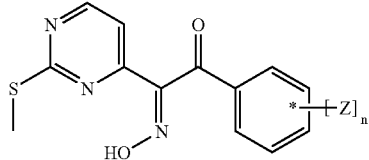
(III)

to produce a compound of the formula

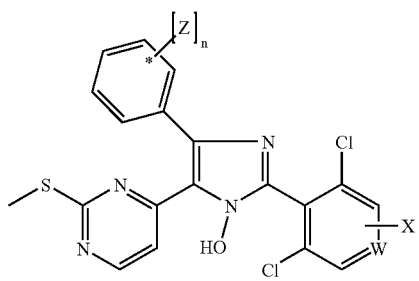
(IV)

which is thereafter N-deoxygenated to produce a compound of the formula

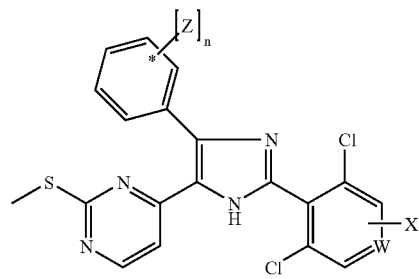
(V)

which is thereafter oxidized via the sulphide group of the thioethers to provide a) compounds of the general formula (VI)

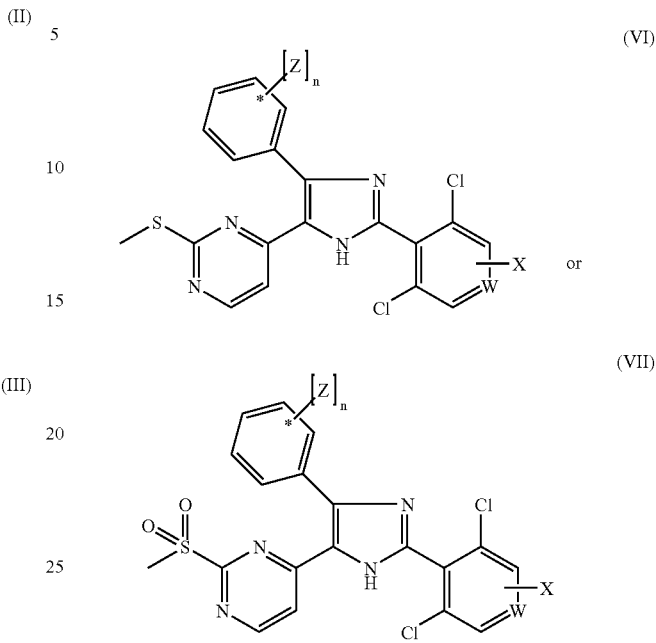
(VI)

or (VII)

which are obtained by N-deoxygenation of compounds of the general formula (IV)

whereby said compounds of the general formula (IV) are obtained by reacting a compound of the general formula (II)

and b) reacting said compounds of the formulae (VI) or (VII) with a compound of the formula Y—NH$_2$ to give the compounds of formula (I); and the substituents W, X, Y and Z as well as n having the significance given in claim 1.

9. A pharmaceutical composition comprising a compound of formula:

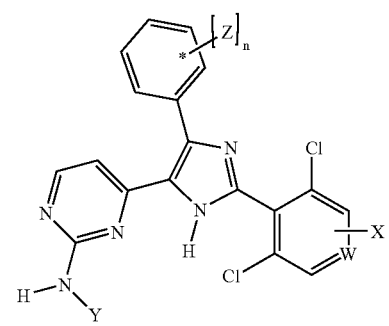
(I)

wherein:
W is —N═;
X is hydrogen;
Y is hydrogen or a group A$^2$—R;

$A^2$ is $C_1$–$C_5$-alkylene, which maybe optionally substituted by C1–$C_6$-alkyl, phenyl or by hydroxy;

R is selected from the group consisting of hydroxy; linear or branched C1–$C_6$-alkoxy; amino; dimethylamino; diethylamino; t-butyloxycarbonylamino; carboxyl; $C_1$–$C_6$-alkoxycarbonyl; triazolyl; cyano; piperidino; 1-pyrrolidinyl; morpholino; 4-methylpiperazin-1-yl; O—$A^1$—$NR^3R^4$; S—$A^1$—$NR^3R^4$; 4-carboxyphenyl; furan-3 yl; thiophen-2yl; and 3-methylthiophen-2yl;

n is 1 or 2; and

Z is one or two substituents independently selected from the group consisting of halogen; hydroxy; allyloxy; methyl; $C_1$–$C_3$-alkoxy, which are optionally substituted with pyridinyl; methoxymethoxy; (2-methoxyethoxy)methyloxy; methylthio; ethoxymethoxy; methylendioxy; ethynyl; trimethylsilylethynyl; benzyloxy which is optionally substituted by halogen; methoxy; cyano; nitro; methylendioxy; carboxy and ethoxy;

or alternatively:

W is —CH═;

X is selected from the group consisting of hydrogen; $OR^1$; $SR^2$; $(SO)R^2$; $(SO_2)R^2$; $CH_2$—S—$CH_2$—$C(O)_2$—$CH_2$—$CH_3$; $CH_2$—S—$(CH_2)_2$—OH; and a group $A^1$—Q;

$A^1$ represents a $C_1$–$C_3$-alkylene group;

Q is selected from the group consisting of $OR^1$; $SR^2$; $SOR^2$; $SO_2R^2$; $NR^3R^{4;\ NHCH}{}_2CH_2NR^3R_4$ and halogen;

$R^1$ is selected from the group consisting of hydrogen; $C_1$–$C_3$-alkyl; allyl; dimethylphosphonylmethyl; 2,3-epoxy-1-propyl; (R)-2,3-dihydroxy-1-propyl; (S)-2,3-dihydroxy-1-propyl; 1,3-dihydroxy-2-propyl; 3-hydroxy-2-hydroxymethyl-1propyl; 2-methoxyethoxymethyl; 2,2-dimethyl-1,3-dioxolan-4-ylmethyl; and a group $A^1$—$Q^1$;

$Q^1$ is selected from the group consisting of $C_1$–$C_2$-alkoxy; cyano; carboxyl; $C_1$–$C_6$-alkoxycarbonyl; carboxamide; —CO—$NR^3R^4$; $C_1$–$C_6$-alkylsulfanyl; $C_1$–$C_6$-alkylsulfenyl; and $C_1$–$C_6$-alkylsulfonyl; except if $A^1$ represents a 1,2-ethylen- or 1,3-propylen group, then $Q^1$ is hydroxy or $NR^3R^4$;

$R^2$ is selected from the group consisting of $C_1$–$C_6$-alkyl; dimethylphosphonylmethyl; 2,3-epoxy-1-propyl; 2,3-dihydroxy-1-propyl; 2,2-dimethyl-1,3-dioxolan-4-ylmethyl; and $A^1$—$Q^1$;

$R^3$ and $R^4$ are independently selected from the group consisting of hydrogen and $C_1$–$C_6$-alkyl; or alternatively $R^3$ and $R^4$ together form a 5 to 7 membered, saturated or unsaturated ring, optionally substituted by a methyl group and containing one or two heteroatoms, independently selected from the group consisting of N and O;

Y is hydrogen or a group $A^2$—R;

$A^2$ is $C_1$–$C_5$-alkylene, which may be optionally substituted by $C_1$–$C_6$-alkyl, phenyl or by hydroxy;

R is selected from the group consisting of hydroxy; linear or branched C1–$C_6$-alkoxy; amino; dimethylamino; diethylamino; t-butyloxycarbonylamino; carboxyl; $C_1$–$C_6$-alkoxycarbonyl; triazolyl; cyano; piperidino; 1-pyrrolidinyl; morpholino; 4-methylpiperazin-1-yl; O—$A^1$—$NR^3R^4$; S—$A^1$—$NR^3R^4$; 4-carboxyphenyl; furan-3-yl; thiophen-2-yl ; and 3-methylthiophen-2-yl;

n is 1 or 2; and Z represents $C_1$–$C_3$-alkoxy, substituted with pyridinyl if n is 1; or alternatively if n is 2, one substituent is $C_1$–$C_3$-alkoxy, substituted with pyridinyl, and the second substituent is independently selected from the group consisting of halogen; hydroxy; allyloxy; methyl; C1–C3-alkoxy; methoxymethoxy; (2-methoxyethoxy)methyloxy; methylthio; ethoxymethoxy; methylendioxy; ethynyl; and trimethylsilylethynyl;

or pharmaceutically acceptable salts thereof together with pharmaceutically acceptable adjuvants.

10. A method of treating colon cancer comprising administering to a patient in need thereof a therapeutically effective amount of a compound of formula:

(I)

wherein:

W is —N═;

X is hydrogen;

Y is hydrogen or a group $A^2$—R;

$A^2$ is $C_1$–$C_5$-alkylene, which may be optionally substituted by $C_1$–$C_6$-alkyl, phenyl or by hydroxy;

R is selected from the group consisting of hydroxy; linear or branched C1–$C_6$-alkoxy; amino; dimethylamino; diethylamino; t-butyloxycarbonylamino; carboxyl; $C_1$–$C_6$-alkoxycarbonyl; triazolyl; cyano; piperidino; 1-pyrrolidinyl; morpholino; 4-methylpiperazin-1-yl; O—$A^1$—$NR^3R^4$; S—$A^1$—$NR^3R^4$; 4-carboxyphenyl; furan-3yl; thiophen-2yl; and 3-methylthiophen-2-yl n is 1 or 2; and Z is one or two substituents independently selected from the group consisting of halogen; hydroxy; allyloxy; methyl; $C_1$–$C_3$-alkoxy, which are optionally substituted with pyridinyl; methoxymethoxy; (2-methoxyethoxy)methyloxy; methylthio; ethoxymethoxy; methylendioxy; ethynyl; trimethylsilylethynyl; benzyloxy which is optionally substituted by halogen; methoxy; cyano; nitro; methylendioxy; carboxy and ethoxy;

or alternatively:

W is —CH═; X is selected from the group consisting of hydrogen; $OR^1$; $SR^2$; $(SO)R^2$; $(SO_2)R^2$; $CH_2$—S—$CH_2$—$C(O)_2$—$CH_2$—$CH_3$; $CH_2$—S—$(CH_2)_2$—OH; and a group $A^1$—Q;

$A^1$ represents a $C_1$–$C_3$-alkylene group;

Q is selected from the group consisting of $OR^1$; $SR^2$; $SOR^2$; $SO_2R^2$; $NR^3R^{4;\ NHCH}{}_2CH_2NR^3R^4$ and halogen;

$R^1$ is selected from the group consisting of hydrogen; $C_1$–$C_3$-alkyl; allyl; dimethylphosphonylmethyl; 2,3-epoxy-1-propyl; (R)-2,3-dihydroxy-1-propyl; (S)-2,3-dihydroxy-1-propyl; 1,3-dihydroxy-2-propyl; 3hydroxy-2-hydroxymethyl-1 -propyl; 2-methoxyethoxymethyl; 2,2-dimethyl-1,3-dioxolan-4-ylmethyl; and a group $A_1$—$Q^1$;

$Q^1$ is selected from the group consisting of $C_1$–$C_2$-alkoxy; cyano; carboxyl; $C_1$–$C_6$-alkoxycarbonyl; carboxamide; —CO—$NR^3R^4$; $C_1$–$C_6$-alkylsulfanyl; $C_1$–$C_6$-alkylsulfenyl; and $C_1$–$C_6$-alkylsulfonyl; except if $A^1$ represents a 1,2-ethylen- or 1,3-propylen group, then $Q^1$ is hydroxy or $NR^3R^4$;

$R^2$ is selected from the group consisting of $C_1$–$C_6$-alkyl; dimethylphosphonylmethyl; 2,3-epoxy-1-propyl; 2,3-dihydroxy-1-propyl; 2,2-dimethyl-1,3-dioxolan-4-ylm-ethyl; and $A^1$—$Q^1$;

$R^3$ and $R^4$ are independently selected from the group consisting of hydrogen and $C_1$–$C_6$-alkyl; or alternatively $R^3$ and $R^4$ together form a 5 to 7 membered, saturated or unsaturated ring, optionally substituted by a methyl group and containing one or two heteroatoms, independently selected from the group consisting of N and O;

Y is hydrogen or a group $A^2$—R;

$A^2$ is $C_1$–$C_5$-alkylene, which may be optionally substituted by $C_1C_6$-alkyl, phenyl or by hydroxy;

R is selected from the group consisting of hydroxy; linear or branched $C_1C_6$-alkoxy; amino; dimethylamino; diethylamino; t-butyloxycarbonylamino; carboxyl; $C_1$–$C_6$-alkoxycarbonyl; triazolyl; cyano; piperidino; 1-pyrrolidinyl; morpholino; 4-methylpiperazin-1-yl; O—$A^1$—$NR^3R^4$; S—A—$NR^3R^4$; 4-carboxyphenyl; furan-3-yl; thiophen-2-yl; and 3-methylthiophen-2-yl;

n is 1 or 2; and

Z represents $C_1$–$C_3$-alkoxy, substituted with pyridinyl if n is 1; or alternatively if n is 2, one substituent is $C_1$–$C_3$-alkoxy, substituted with pyridinyl, and the second substituent is independently selected from the group consisting of halogen; hydroxy; allyloxy; methyl; $C_1$–$C_3$-alkoxy; methoxymethoxy; (2-methoxyethoxy) methyloxy; methylthio; ethoxymethoxy; methylendioxy; ethynyl; and trimethylsilylethynyl;

or pharmaceutically acceptable salts thereof.

* * * * *

UNITED STATES PATENT AND TRADEMARK OFFICE
CERTIFICATE OF CORRECTION

PATENT NO. : 7,144,889 B2  Page 1 of 3
APPLICATION NO. : 10/959849
DATED : December 5, 2006
INVENTOR(S) : Thomas von Hirschheydt et al.

It is certified that error appears in the above-identified patent and that said Letters Patent is hereby corrected as shown below:

Title Page, Item (73) Assignee: delete "Hoffman-La Roche Inc., Nutley, NJ (US)" and insert -- Hoffmann-La Roche Inc., Nutley, NJ (US) --

Column 23, Claim 2, line 53, delete "n is 1 and Z is selected from the group consisting of" and insert -- n is 1; and
    Z is selected from the group consisting of --

Column 24, Claim 5, line 36, delete "ethyl; and A1-Q1; R3 and R4 are independently" and insert -- ethyl; and A1-Q1;
    R3 and R4 are independently --

Column 25, Claim 7, lines 31-35, delete "lamino]-4-yl-N-1H-imidazole;    2(2,6-Dichloro-4[2-hydroxyethoxy]phenyl-4(3 (3pyridinylmethoxy)-phenyl)    -5(2-[3-Hydroxypropylamino]pyrimidin-4-yl)-N-1H-" and insert
-- lamino]-4-yl-N-1H-imidazole;
  2(2,6-dichloro-4-[2-hydroxyethoxy]phenyl-4-(3-(3-pyridinylmethoxy)-phenyl)-5(2-
  [3-hydroxypropylamino]pyrimidin-4-yl)-N-1H- --

Column 26, Claim 8, lines 25-27, delete "dihydroxy-1-propyl; 1,3-dihydroxy-2propyl; 3-hydroxy-2-hydroxymethyl-1-propyl; 2methoxyethoxymethyl;" and insert
-- dihydroxy-1-propyl; 1,3-dihydroxy-2-propyl; 3-hydroxy-2-hydroxymethyl-1-
  propyl; 2-methoxyethoxymethyl; --

Column 28, Claim 8, lines 5-15, delete

" 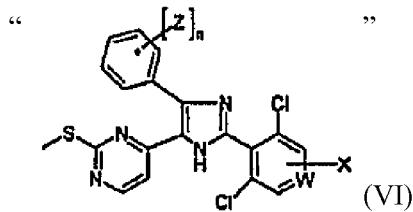 "

and insert

-- 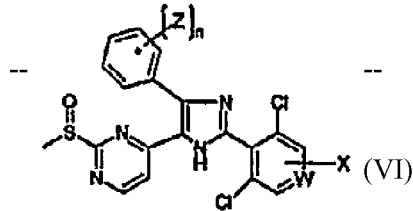 --

UNITED STATES PATENT AND TRADEMARK OFFICE
CERTIFICATE OF CORRECTION

PATENT NO. : 7,144,889 B2
APPLICATION NO. : 10/959849
DATED : December 5, 2006
INVENTOR(S) : Thomas von Hirschheydt et al.

It is certified that error appears in the above-identified patent and that said Letters Patent is hereby corrected as shown below:

Column 29, Claim 9, line 27, delete "$SOR^2$; $SO_2R^2$; $NR^3R^{4;\ NHCH}{}_2CH_2NR^3R_4$" and insert -- $SOR^2$; $SO_2R^2$; $NR^3R^4$; $NHCH_2CH_2NR^3R^4$ --

Column 29, Claim 9, line 62, delete:

"n is 1 or 2; and Z represents $C_1$-$C_3$-alkoxy, substituted
    with pyridinyl if n is 1; or alternatively
if n is 2,"

and insert:

-- n is 1 or 2; and
Z represents $C_1$-$C_3$-alkoxy, substituted with pyridinyl if n is 1; or alternatively if n is 2, --

Column 30, Claim 10, line 38, delete "furan-3yl; thiophen-2yl;" and insert -- furan-3-yl; thiophen-2-yl; --

Column 30, Claim 10, line 50, delete:

"W is –CH=; X is selected from the group consisting of"

and insert:

-- W is –Ch=;
X is selected from the group consisting of --

Column 30, Claim 10, line 56, delete "$SOR^2$; $SO_2R^2$; $NR^3R^{4;\ NHCH}{}_2CH_2NR^3R^4$" and insert -- $SOR^2$; $SO_2R^2$; $NR^3R^4$; $NHCH_2CH_2NR^3R^4$ --

UNITED STATES PATENT AND TRADEMARK OFFICE
CERTIFICATE OF CORRECTION

PATENT NO. : 7,144,889 B2
APPLICATION NO. : 10/959849
DATED : December 5, 2006
INVENTOR(S) : Thomas von Hirschheydt et al.

It is certified that error appears in the above-identified patent and that said Letters Patent is hereby corrected as shown below:

Column 30, Claim 10, line 61, delete "3hydroxy-2-hydroxymethyl-1-" and insert -- 3-hydroxy-2-hydroxymethyl-1- --

Signed and Sealed this

Second Day of October, 2007

JON W. DUDAS
*Director of the United States Patent and Trademark Office*